US008294733B2

(12) United States Patent
Eino

(10) Patent No.: US 8,294,733 B2
(45) Date of Patent: Oct. 23, 2012

(54) ENDOSCOPIC IMAGE VIEWING PROGRAM AND METHOD

(75) Inventor: Teruo Eino, Hachioji (JP)

(73) Assignee: Olympus Corporation, Tokyo (JP)

( * ) Notice: Subject to any disclaimer, the term of this patent is extended or adjusted under 35 U.S.C. 154(b) by 790 days.

(21) Appl. No.: 12/136,022

(22) Filed: Jun. 9, 2008

(65) Prior Publication Data
US 2008/0304724 A1    Dec. 11, 2008

(30) Foreign Application Priority Data

Jun. 8, 2007  (JP) ................................. 2007-152827
Jun. 8, 2007  (JP) ................................. 2007-152911
Jun. 8, 2007  (JP) ................................. 2007-152990

(51) Int. Cl.
*G09G 5/00*    (2006.01)
(52) U.S. Cl. ........................................ 345/629; 345/684
(58) Field of Classification Search .................. 345/629, 345/684
See application file for complete search history.

(56) References Cited

U.S. PATENT DOCUMENTS

| | | | | |
|---|---|---|---|---|
| 5,740,801 A * | 4/1998 | Branson | ......................... | 600/407 |
| 6,262,728 B1 * | 7/2001 | Alexander | ................. | 345/440.1 |
| 6,320,577 B1 * | 11/2001 | Alexander | ................. | 345/440.1 |
| 6,661,571 B1 * | 12/2003 | Shioda et al. | .................. | 359/372 |
| 7,119,814 B2 * | 10/2006 | Meron et al. | .................... | 345/619 |
| 7,564,626 B2 * | 7/2009 | Bendall et al. | ................. | 359/462 |
| 7,706,588 B2 * | 4/2010 | Matsumoto | .................... | 382/128 |
| 7,831,294 B2 * | 11/2010 | Viswanathan | ................ | 600/425 |
| 2002/0030683 A1 * | 3/2002 | Alexander | ................. | 345/440.1 |
| 2002/0057828 A1 * | 5/2002 | Oosawa et al. | ............... | 382/132 |
| 2003/0188305 A1 | 10/2003 | Morimoto | | |
| 2004/0070822 A1 * | 4/2004 | Shioda et al. | ................. | 359/372 |
| 2006/0079745 A1 * | 4/2006 | Viswanathan | ................ | 600/407 |
| 2007/0165306 A1 * | 7/2007 | Bendall et al. | ................. | 359/464 |
| 2007/0273757 A1 * | 11/2007 | Mader et al. | ..................... | 348/36 |
| 2008/0091069 A1 * | 4/2008 | Groszmann | ................... | 600/117 |

FOREIGN PATENT DOCUMENTS

| | | |
|---|---|---|
| JP | 2003-256210 A | 9/2003 |
| JP | 2006-334247 A | 12/2006 |
| JP | 2006-350634 A | 12/2006 |

* cited by examiner

*Primary Examiner* — M Good Johnson
(74) *Attorney, Agent, or Firm* — Holtz, Holtz, Goodman & Chick, PC

(57) ABSTRACT

A computer is caused to perform a process for displaying an endoscopic image, including displaying an endoscopic image on a display, displaying overlay information on the displayed endoscopic image, and changing a position of the displayed overlay information in accordance with a change in the displaying of the endoscopic image.

25 Claims, 28 Drawing Sheets

ENDOSCOPIC IMAGE VIEWING PROGRAM AND METHOD

CROSS-REFERENCE TO RELATED APPLICATIONS

This application is based on Japanese patent applications No. 2007-152827, No. 2007-152990, No. 2007-152778, No. 2007-152911 and No. 2007-141599, the entire contents of all of which are incorporated herein by reference.

BACKGROUND OF THE INVENTION

1. Field of the Invention

The present invention relates to an endoscopic image display apparatus and an endoscopic image viewing program for viewing image data taken by an endoscopic device.

2. Description of the Related Art

Conventionally, in order to view an image taken by an endoscopic device, for example, an endoscopic image viewing program for viewing endoscopic images is installed in a personal computer and executed by the personal computer. The image to be viewed is stored in a recording medium such as a memory card by the endoscopic device (see, for example, JP 2006-334247 A).

Various incidental information relating to the taking of the image is stored together with the image in the recording medium. For example, the incidental information relating to taking of the image includes a file name of an image file of the image, a date and time of image recording, an image-taking condition, the name of an optical adapter used (at the distal end of an endoscope) to take the image, and measurement data in the image. The endoscopic image viewing program is thus able to display the image as well as the incidental information.

Conventionally, it has been possible with a conventional endoscopic image viewing program to display two images simultaneously, by displaying the images in respective windows with a window display one image overlaid on a window displaying the other image, or by reducing the size of the two images and displaying the images side by side.

FIG. 1 shows a conventional example of two windows each displaying an image in an overlaid state. In FIG. 1, both an image window 101 in which an image 102 is displayed, and an image window 103 in which an image 104 is displayed, are opened and displayed on a display screen 105. In the example shown in FIG. 1, the image window 103 is overlaid on the image window 101. However, when two images taken by the endoscopic device are displayed, with one image overlaid on another image, there has been a problem that a manipulation has to be executed so that the image that is desired to be viewed is displayed on top. In particular, when two images are being compared to each other, it is necessary to repeatedly change which image is on top, which complicates the comparison.

FIG. 2 shows a conventional example of two images that are reduced in size and displayed side by side. In FIG. 2, the images 102 and 104 are displayed in a reduced size in image window 106 so that each of the images 102 and 104 can be displayed in its entirety. However, when two images are reduced in size to be displayed side by side, there has been a problem that the detail in each image is reduced, and is insufficient.

It has also been possible with a conventional endoscopic image viewing program to display a stereoscopic image, which has been taken stereoscopically by the endoscope. However, when the displayed image is a stereoscopic image, for example for performing measurement, two images with almost no difference are displayed at the same time, which may be unnecessary in viewing or utilizing the image with another application program or device.

With the endoscopic image display technique described above, since the image file and the incidental information relating thereto are stored separately, that is, as separate files, the image and the incidental information are separately displayed, for example, in separate windows. Therefore, there has been a problem that, for example, it is difficult to understand what part of the image is indicated by the incidental information. In addition, when both the image and the incidental information are to be utilized using a different kind of application program or device, there has been a problem that manipulation is complicated due to the necessity of handling each of the image and the incidental information as a separate file.

The endoscopic image display technique described above is also capable of displaying an image and incidental information in an overlaid state. However, in this case, it is necessary to create and store one item of data, that is, one file, in which the image and the incidental information are overlaid. As a result, there has been a problem that it is not possible to cause the image to be displayed by itself at a later time.

In a conventional information display apparatus, for example, a device such as a personal computer having image display software installed thereon, creates a folder or a directory and stores each electronic file in the folder, to classify and arrange an electronic document file and an electronic file such as an electronic image file on a storage medium (storage device). Sub-folders can be provided in the folder in addition to the electronic files. The folder or directory, sub-folder or sub-directory, and electronic files are usually classified and managed hierarchically. The folders and sub-folders, which are classified and managed hierarchically, are usually also displayed hierarchically in a predetermined region so that the hierarchical structure may be easily identified visually. And the sub-folders or electronic files stored in an arbitrary designated folder or sub-folder may be displayed in a list in a predetermined region. (See, for example, JP 2006-350634 A.)

FIG. 3 is an example of display of thumbnail images by a conventional information display apparatus. As shown in FIG. 3, the conventional information display apparatus displays a main window 111 as a display window on a display screen 110. The main window 111 includes a toolbar 112 (of various types), as well as a folder tree area 113 and a contents area 114 in addition to a toolbar 12. The folder tree area 113 and the contents area 114 are displayed simultaneously. In the example shown in FIG. 3, the hierarchically managed folders and files are displayed in the folder tree area 113, and a folder is highlighted to show that it is designated (see the folder named "1001V7R1"). Moreover, a limited number (nine) of the electronic files in the folder ("1001V7R1") designated in the folder tree area 113 are displayed in thumbnail format in the contents area 114.

FIG. 4 is similar to FIG. 3, except that the electronic files in the folder ("1001V7R1") designated in the folder tree area 113 are displayed as a list of file names, instead of as thumbnails, in the contents area 114. The user can switch between the views used in the contents area 114 in FIGS. 3 and 4 using the toolbar 112.

The display in the thumbnail format shown in the contents area 114 in FIG. 3 is convenient because it allows the user to know what kind of image each file is. However, because of the screen area occupied by each thumbnail, the number of thumbnails that can be displayed in the contents area 114 is very limited, and in many cases, all of the electronic files in the designated folder cannot be displayed. In this case, the thumbnails of all of the electronic files can be displayed sequentially by manipulating a scrollbar. Moreover, even though the performance of modern computers has been enhanced, because each thumbnail is an image, displaying a plurality of thumbnails requires a certain amount of time. Therefore, if a user wants to execute a specific electronic file and the thumbnail of the electronic file is not currently displayed in the contents area 114, the thumbnails must be scrolled through unit the desired electronic file is displayed. Thus, the user must wait for the time required for processing by the personal computer in this operation.

When the display in the contents area 114 is shifted to a list display of the file names as shown in FIG. 4, the display of the file names is completed almost instantaneously. In addition, even if a large number of electronic files are stored in the designated folder, a large number of file names can be displayed at one time in list form, because the area occupied by one file name is small. Still further, even if all of the electronic files stored in the designated folder cannot be displayed at one time and thus have to be scrolled by displaying a scrollbar, the scrolling will be performed at a high speed. Therefore, while a user may not know what each file is in the case that the list display of the file names as shown in FIG. 4 is used, if the user desires to execute a certain electronic file, the motion can be executed in a very short time.

With the conventional image display apparatus described above, when a list of sub-folders or electronic files stored in a designated folder or sub-folder is displayed in a predetermined region, the list may be a list of a limited number of thumbnails, icons or the like, or may be a list of a large number of file names without thumbnails, depending the purpose of use by the user. Consequently, there has been a problem that simultaneously performing display of the thumbnail list and display of the file name list is not possible.

Conventionally, moreover, it has been necessary to install an endoscopic image viewing program on a personal computer, for example, to view an image taken by an endoscopic device. FIG. 5 illustrates a conventional endoscope system, and FIG. 6 is illustrates installation of the conventional endoscopic image viewing program.

In FIG. 5, an endoscope system 200 for the purpose of inspecting, for example, a blade of an aircraft engine or an internal area of electric wiring includes an industrial endoscopic device 210 to observe an internal area of a machine or a lumen that is difficult to access and a personal computer 220 with an endoscopic image viewing program 222 installed on a hard disk 221 thereof. The endoscopic image viewing program 222 is executed by the personal computer 220 to view image data 212 captured by the endoscopic device 210. The image data 212 captured by the endoscopic device 210 is transmitted to the personal computer 220 using a memory card 211 or a USB cable 240.

In order to enable viewing of the image data 212 by executing the endoscopic image viewing program 222, a CPU 225, which is interconnected with the hard disk 221 and a RAM 224 via a bus 223, reads out the endoscopic image viewing program 222 from the hard disk 221 onto the RAM 224 and executes the endoscopic image viewing program 222.

In order to provide the endoscope system 200 shown in FIG. 5, the endoscopic image viewing program 222 needs to be installed in the personal computer 220. Installation is performed by executing an installation program 231 (hereinafter called the installer) for installing the endoscopic image viewing program 222, by deploying an endoscopic image display application 232 to the personal computer 220 to be stored in the personal computer 220 as the endoscopic image viewing program 222. The endoscopic image display application 232 herein is a file set which is not executable by itself, and the endoscopic image viewing program 222 is a self-executable execution module.

Conventionally, as shown in FIG. 6, the endoscopic image display application 232 and the installer 231 have been provided by using a recording medium such as a CD-ROM 230 having the endoscopic image display application 232 and the installer 231 stored thereon, or by enabling downloading of the endoscopic image display application 232 and the installer 231 from a site 260 on a communication network via Internet 250, for example. (See, for example, JP 2003-256210 A.)

However, it is difficult for a user who is not familiar with the operation of personal computers to install an endoscope image viewing program on a personal computer. In addition, in the case of a personal computer owned by a company or other organization, installation of an external application program such as an endoscopic image viewing program may be restricted.

SUMMARY OF THE INVENTION

According to one aspect of the present invention, a computer readable recording medium is provided which has a computer program stored thereon that is executable by a computer to cause the computer to perform a process including: displaying an endoscopic image on a display; displaying overlay information on the displayed endoscopic image; and changing a position of the displayed overlay information in accordance with a change in the displaying of the endoscopic image.

According to another aspect of the present invention, a computer readable recording medium is provided which has a computer program stored thereon that is executable by a computer to cause the computer to perform a process including: displaying an endoscopic image on a display; displaying overlay information on the displayed endoscopic image; and changing the display of the overlay information in accordance with a change in a selection state of the endoscopic image.

According to a further aspect of the present invention, a computer readable recording medium is provided which has a computer program stored thereon that is executable by a computer to cause the computer to perform a process including: displaying at least one endoscopic image on a display; and displaying overlay information on the at least one displayed endoscopic image; wherein the displaying of the overlay information comprises displaying the overlay information at a first predetermined position when a plurality of endoscopic images are displayed, and displaying the overlay information at a second predetermined position when only one endoscopic image is displayed.

According to still another aspect of the present invention, a method is provided which includes displaying an endoscopic image on a display; displaying overlay information on the displayed endoscopic image; and changing a position of the displayed overlay information in accordance with a change in the displaying of the endoscopic image.

DETAILED DESCRIPTION

FIGS. 7-10 illustrate an endoscopic image viewing apparatus and the installation of an endoscopic image viewing program.

Figure 1:
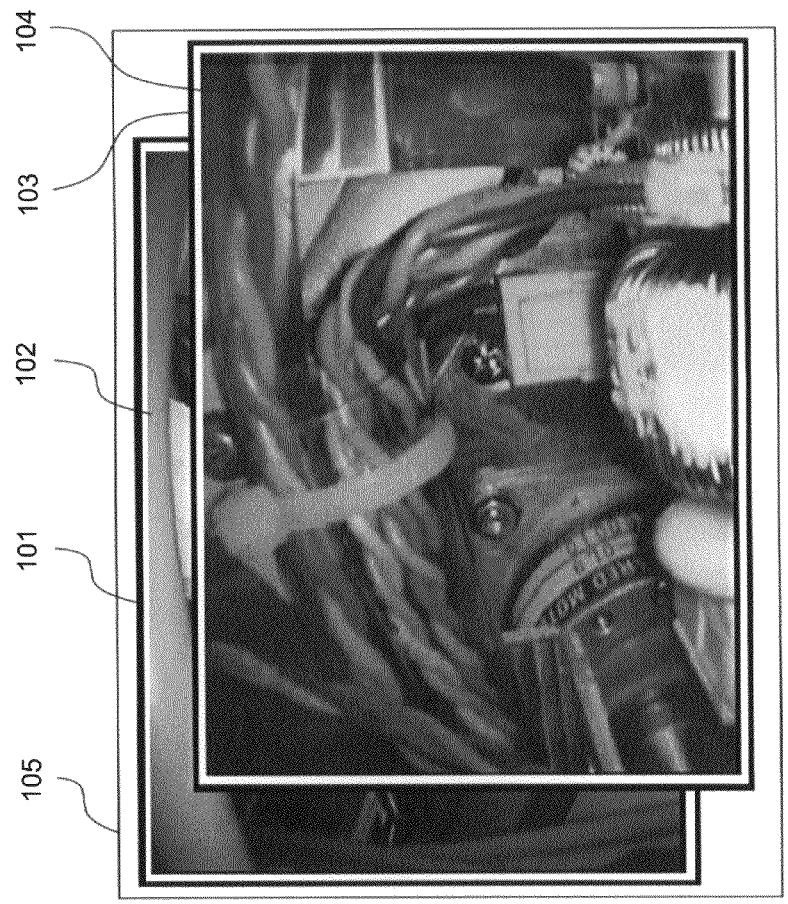
FIG. 1 shows a conventional example of two windows each displaying an image in an overlaid state.
Figure 2:
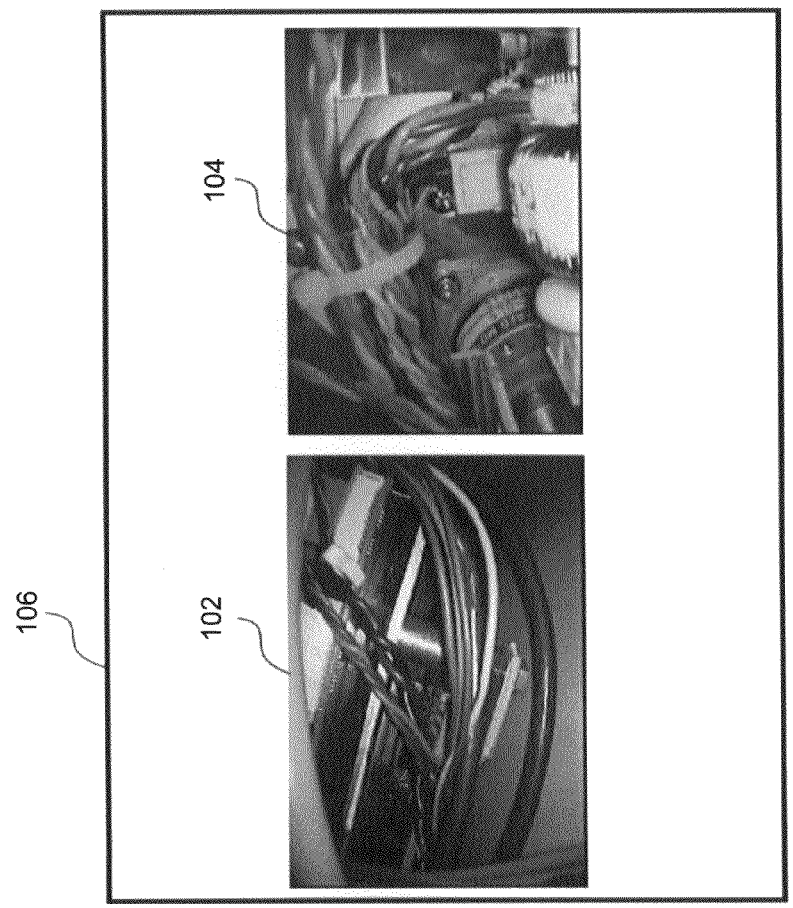
FIG. 2 shows a conventional example of two images that are reduced in size and displayed side by side.
Figure 3:
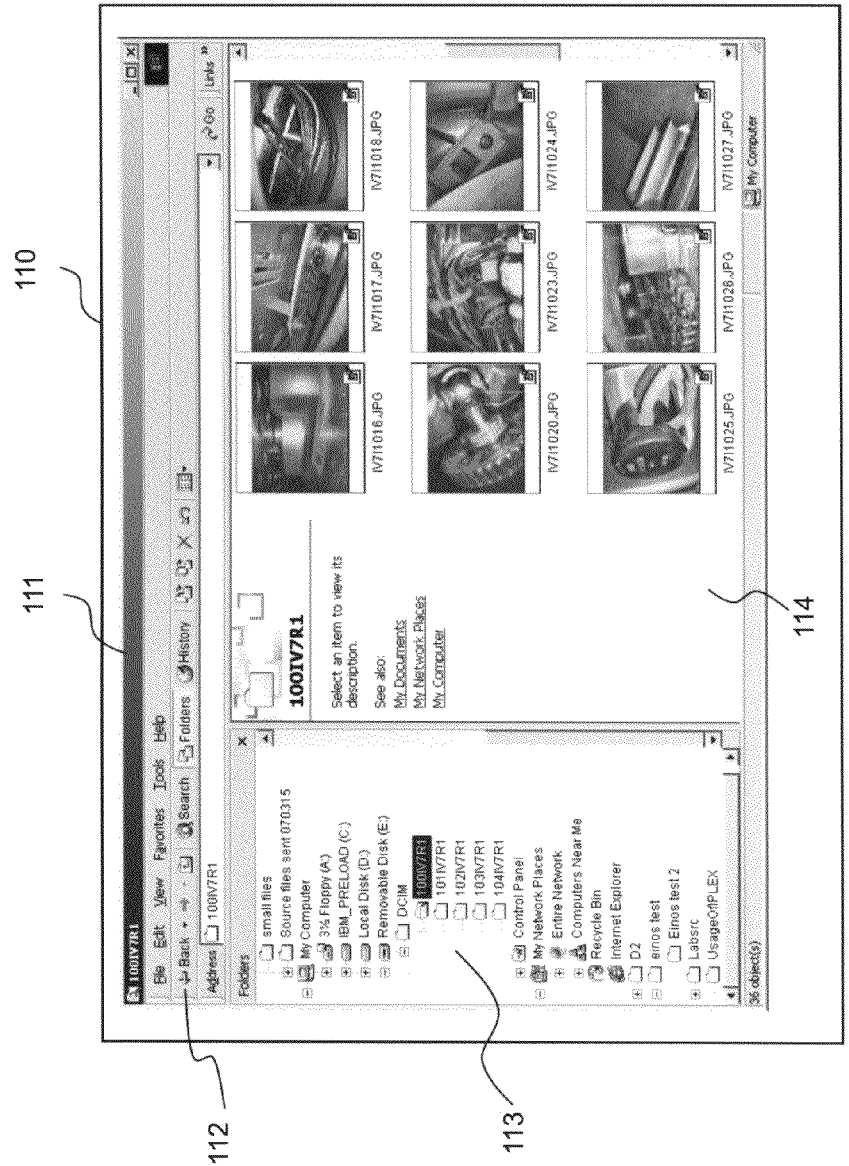
FIG. 3 an example of display of thumbnail images by a conventional information display apparatus.
Figure 4:
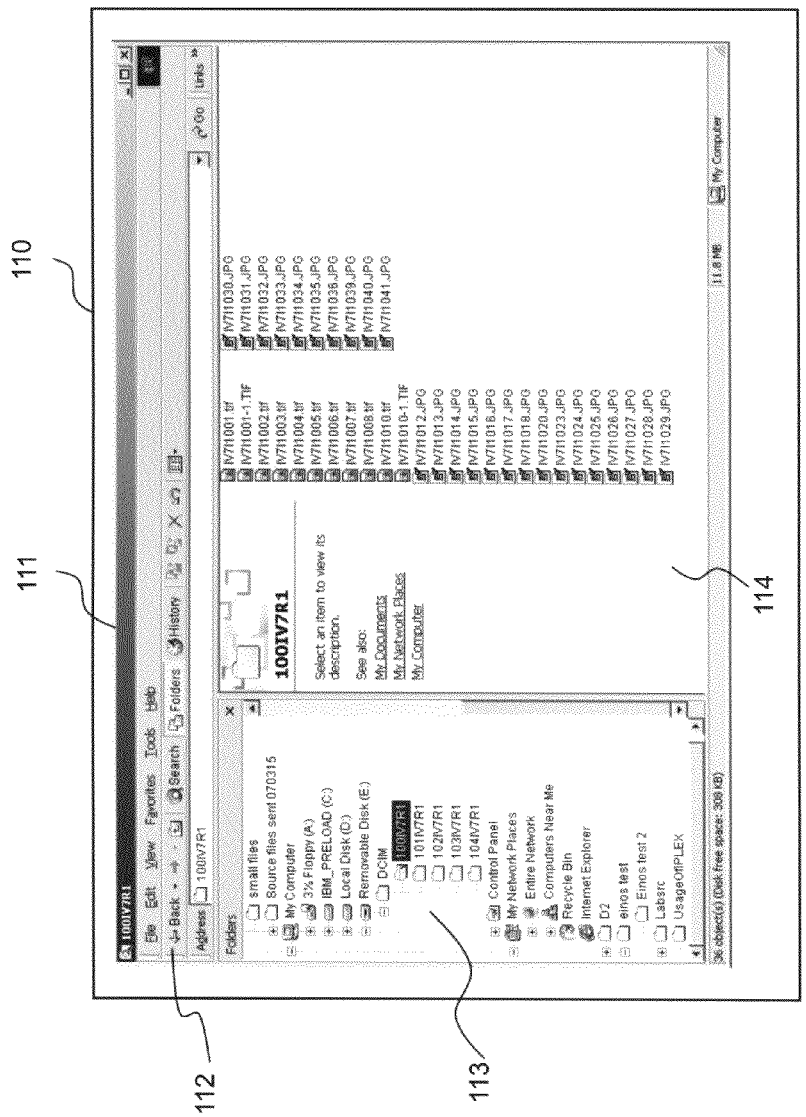
FIG. 4 an example of display of a list of file names by a conventional information display apparatus.
Figure 5:
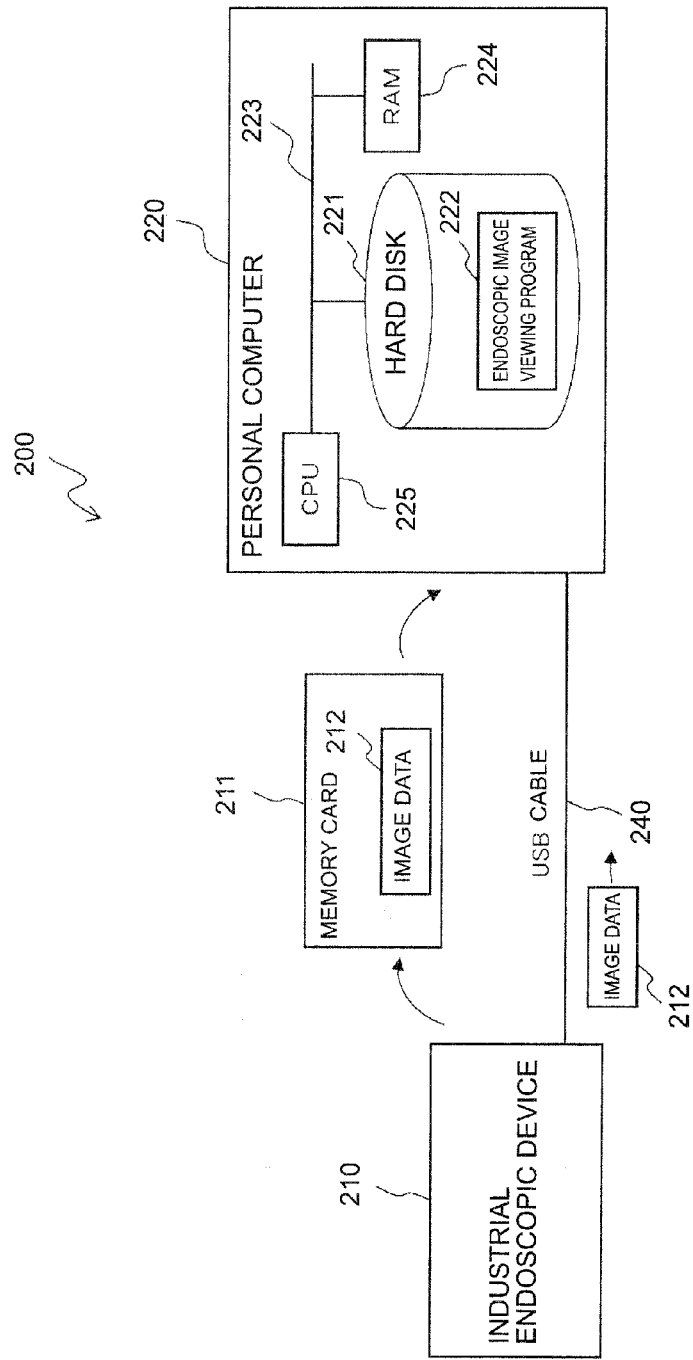
FIG. 5 illustrates a conventional endoscope system.
Figure 6:
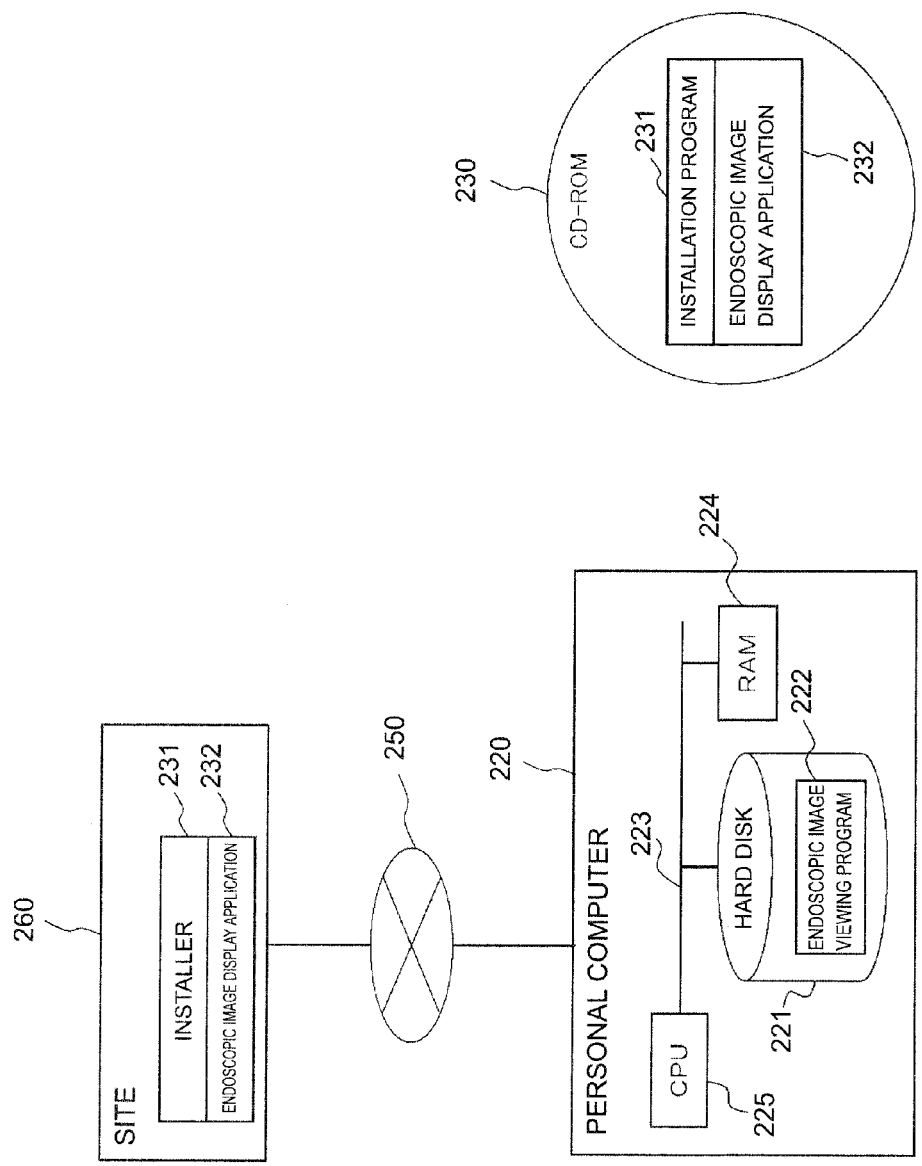
FIG. 6 is illustrates installation of a conventional endoscopic image viewing program in the conventional endoscope system.
Figure 7:
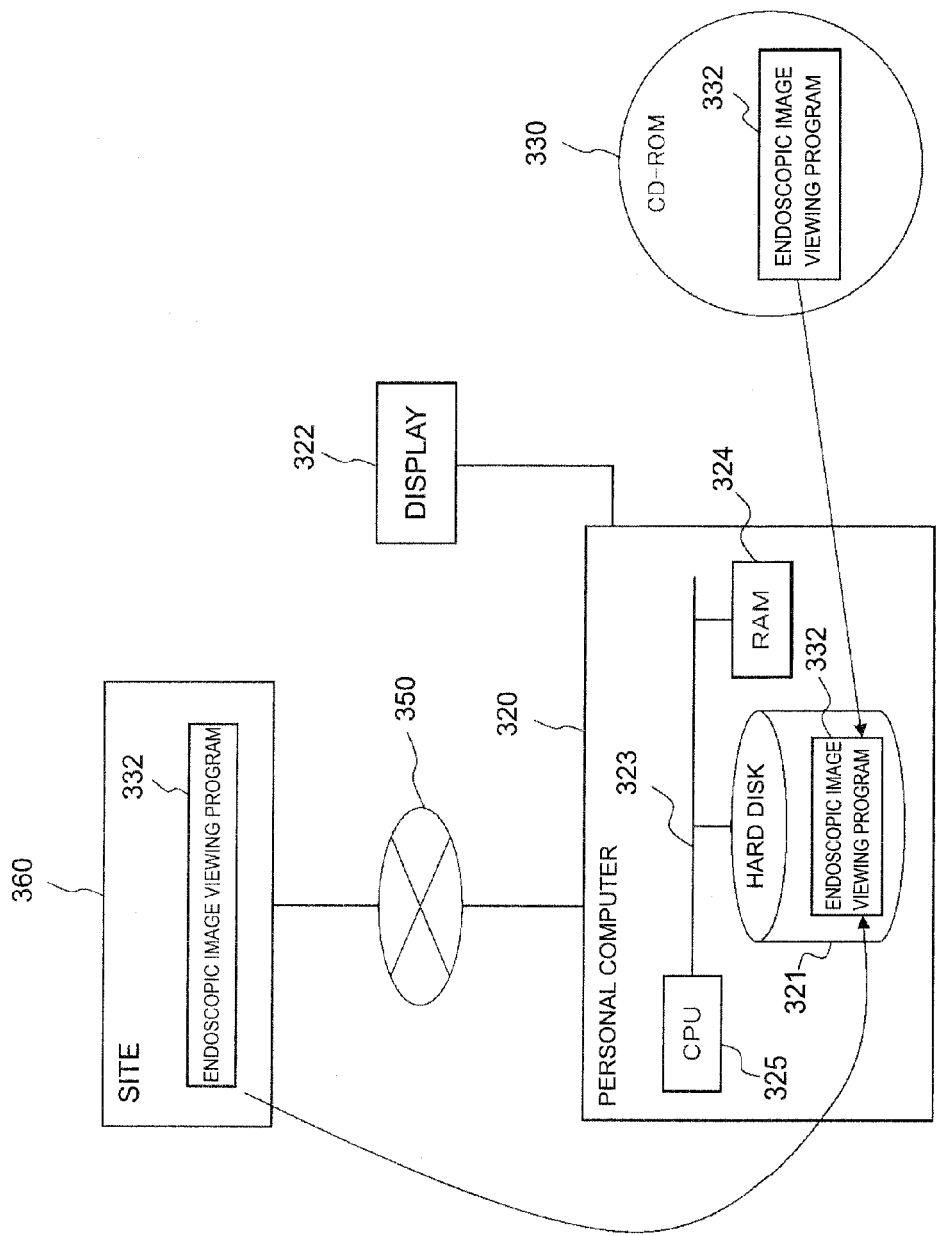
FIG. 7 illustrates an endoscopic image viewing apparatus and structures for proving an endoscopic image viewing program to the endoscopic image viewing apparatus.

As shown in FIG. 7 (see also FIGS. 8-10 with respect to structures relating to FIG. 7 described below), an endoscopic image viewing apparatus is, for example, a personal computer 320, having a hard disk 321, a RAM 324 and a CPU 325, which are connected to each other via a bus 323. The personal computer 320 is coupled to a display 322, via which viewing of endoscopic images using the endoscopic image viewing program is performed.

The endoscopic image viewing program 332 is provided for viewing endoscopic image data 312 of, for example, an inside of an object to be observed, which is captured by an endoscopic device 310. The endoscopic image viewing program 332 is provided in the stored state as an executable module on a portable recording medium such as a CD-ROM 330 (the portable recording medium is not limited to a CD-ROM and may one of various kinds of known portable recording media). Alternatively, an endoscopic image viewing program 332 may be stored on a predetermined site 360, thus being provided as an executable module over Internet 350. That is, the endoscopic image viewing program 332 is merely a data file, like the image data 312 stored on a recording medium such as a memory card 311. Therefore, the endoscopic image viewing program 332 can be duplicated or downloaded, without any particular restriction, on an auxiliary storage device such as a hard disk 321 or a flash memory included in the personal computer 320. The CPU 325 enables viewing of the image data 312 by reading out the endoscopic image viewing program 332 from the hard disk 321 to the RAM 324 and executing the endoscopic image viewing program 332.

Figure 8:
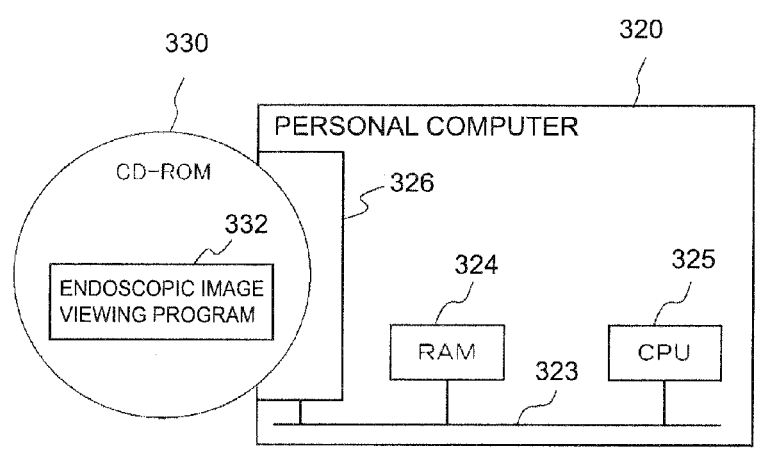
FIG. 8 illustrates another structure for providing the endoscopic image viewing program to the endoscopic image viewing apparatus.

FIG. 8 illustrates another structure for providing the endoscopic image viewing program 332 to the personal computer 320. More specifically, as shown in FIG. 8 (see also FIGS. 7, 9 and 10 with respect structure relating to FIG. 8 described below), the endoscopic image viewing program 332 is stored on a portable recording medium such as the CD-ROM 330 as an executable module, in the same manner as described above. The endoscopic image viewing program 332 is read out from the portable recording medium, such as a CD-ROM 330 by a portable recording medium drive 326, such as a CD-ROM drive of the personal computer 320, without any particular restriction in the state stored on the CD-ROM 330 as it is. More specifically, the CPU 325 is interconnected with the portable recording medium drive 326 and the RAM 324 over the bus 323, and the CPU 325 enables viewing of the image data 312 by driving the portable recording medium drive 326 to read out the endoscopic image viewing program 332, in the state stored as it is on the CD-ROM 330, from the CD-ROM 330 onto the RAM 324 and executing the read out endoscopic image viewing program 332.

Figure 9A:
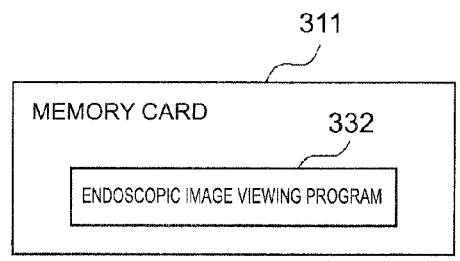
FIGS. 9A, 9B and 9C illustrate another structure for providing the endoscopic image viewing program to the endoscopic image viewing apparatus.
Figure 9B:
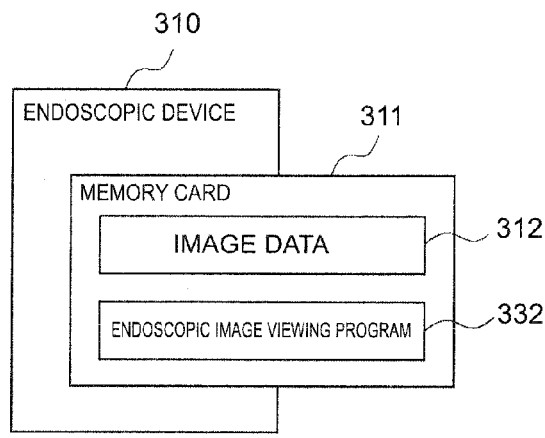
Figure 9C:
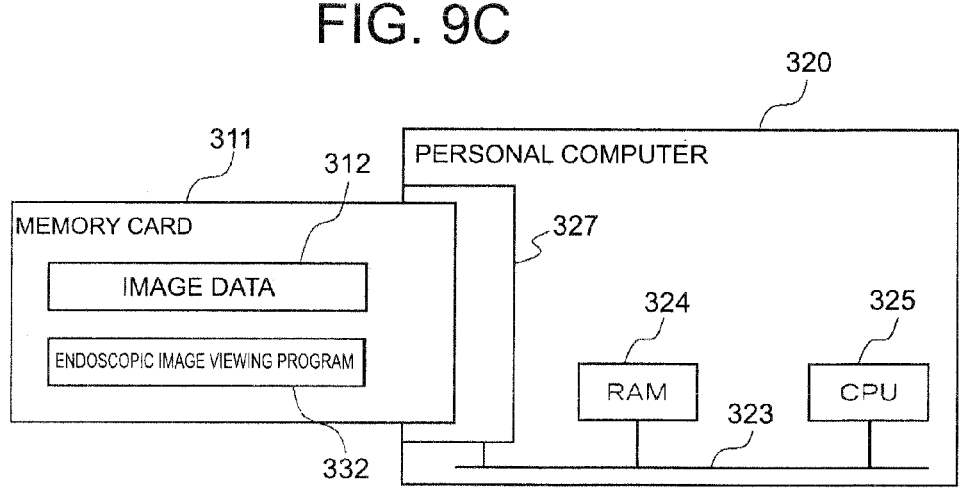

FIGS. 9A, 9B, and 9C illustrate another structure for providing the endoscopic image viewing program 332 to the personal computer 320. More specifically, as shown in FIG. 9A, the endoscopic image viewing program 332 is stored in advance as an executable module on a portable recording medium such as the memory card 311. The endoscopic device 310 records the image data 312 on the memory card 311 when the memory card 311 is coupled to the endoscopic device 310 as shown in FIG. 9B. As shown in FIG. 9C, moreover, the memory card 311 is coupled to the personal computer 320, and the CPU 325 reads out the endoscopic image viewing program 332, in the state stored as it is on the memory card 311, from the memory card 311 onto the RAM 324 via a recording medium drive 327 (to which the CPU 325 is connected via bus 323) of the personal computer 320, and executes the endoscopic image viewing program 332 to enable viewing of the image data 312 on the memory card 311.

Instead of reading out the endoscopic image viewing program 332 directly from the memory card 311 to the RAM 324, the CPU 325 may copy the endoscopic image viewing program 332 (as it is, stored on the memory card 311) from the memory card 311 to the hard disk 321 (along the lines shown in FIG. 7, in which the endoscopic image viewing program 332 is copied from the CD-ROM 330 to the hard disk 321). The CPU 325 may then read the endoscopic image viewing program 332 from the hard disk 321 onto the RAM 324 and execute the endoscopic image viewing program 332. Thus, in this case also, the endoscopic image viewing program 332 is not installed on the personal computer 320.

Figure 10A:
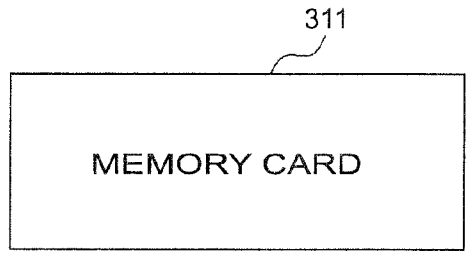
FIGS. 10A, 10B and 10C illustrate another structure for providing the endoscopic image viewing program to the endoscopic image viewing apparatus.
Figure 10B:
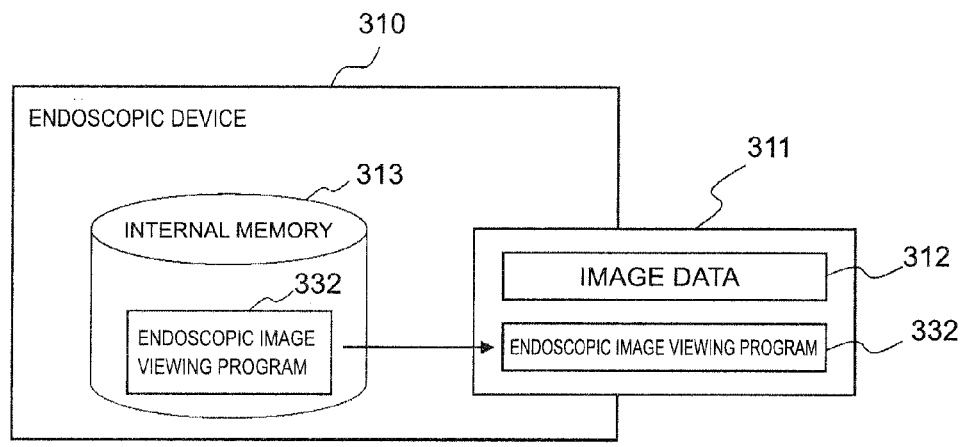
Figure 10C:
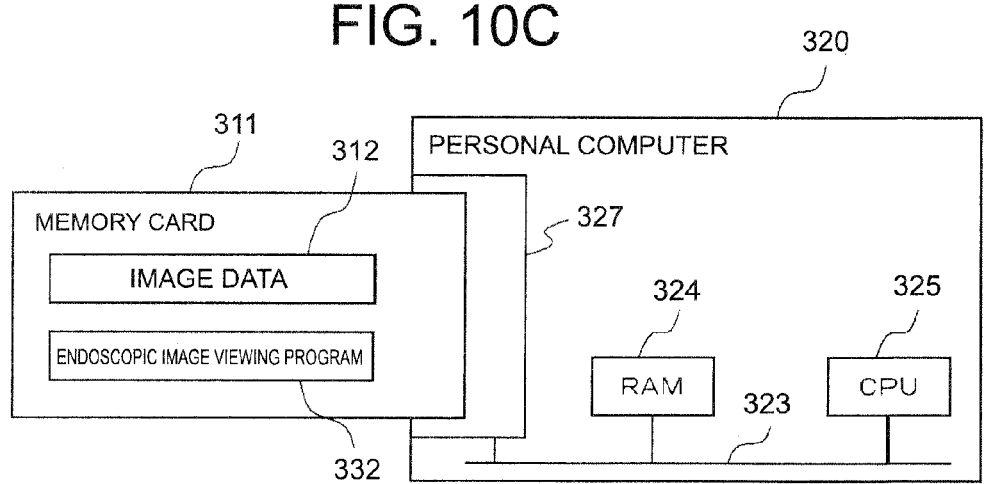

FIGS. 10A, 10B and 10C illustrate another structure for providing the endoscopic image viewing program 332 to the personal computer 320. In contrast to the structure shown in FIG. 9A, in the structure shown in FIG. 10A, the portable recording medium such as the memory card 311 does not have the endoscopic image viewing program 332 stored thereon in advance. As shown in FIG. 10B, the endoscopic device 310 stores the endoscopic image viewing program 332 in an internal memory 313 of the endoscopic device 310 as an executable module in the same manner as described above. The memory card 311 is coupled to the endoscopic device 310, and the endoscopic device 310 copies the image data 312 and the endoscopic image viewing program 332 to the memory card 311. As shown in FIG. 10C, moreover, the memory card 311 is coupled to the personal computer 320, and the CPU 325 reads out the endoscopic image viewing program 332, in the state stored as it is on the memory card 311, from the memory card 311 onto the RAM 324 via a recording medium drive 327 (to which the CPU 325 is connected via bus 323) of the personal computer 320, and executes the endoscopic image viewing program 332 to enable viewing of the image data 312 on the memory card 311.

Instead of reading out the endoscopic image viewing program 332 directly from the memory card 311 to the RAM 324, the CPU 325 may copy the endoscopic image viewing program 332 (as it is, stored on the memory card 311) from the memory card 311 to the hard disk 321 (along the lines shown in FIG. 7, in which the endoscopic image viewing program 332 is copied from the CD-ROM 330 to the hard disk 321). The CPU 325 may then read the endoscopic image viewing program 332 from the hard disk 321 onto the RAM 324 and execute the endoscopic image viewing program 332. Thus, in this case also, the endoscopic image viewing program 332 is not installed on the personal computer 320.

FIGS. 11-17 illustrate the display and execution of electronic files by the endoscopic image viewing program 332. When executed by the personal computer 320 (by the CPU 325 of the personal computer 320), as described above, the endoscopic image viewing program 332 causes the personal computer 320 to display, on the display 322, a main window 411 on the display screen 410 of the display 322.

Figure 11:
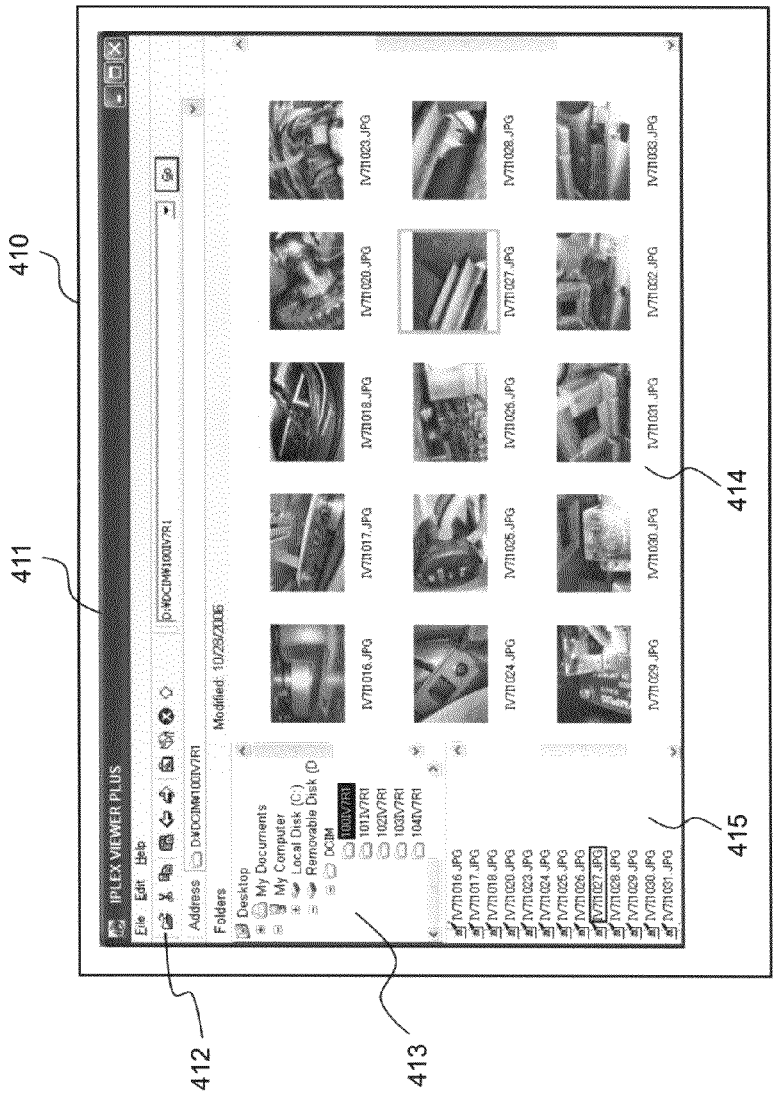
FIG. 11 illustrates a main window displayed when the endoscopic image viewing program is executed.

As shown in FIG. 11, the main window 411 includes a folder tree area 413, a thumbnail area 414, and a file area 415, in addition to the toolbar 412. The toolbar 412, folder tree area 412, thumbnail area 414 and file area 415 are displayed simultaneously in the main window 411. Folders and sub-folders managed hierarchically are displayed in the folder tree area 413 (the folders and sub-folders illustrate conceptual regions where an electronic file or files are recorded on a storage medium). The name of a folder which is currently designated is highlighted (see folder "1001V7R1"). A list of electronic files ("electronic file" is used herein to designate an electronic document or image file that is capable of being processed on a computer such as a personal computer) in the designated folder is displayed as a list of thumbnail images (thumbnail format) in the thumbnail area 414. The list of electronic files in the designated folder is displayed as a list of file names (file name format) in the file area 415.

The boundaries between the folder tree area 413, the thumbnail area 414 and the file area 415 may be adjusted (moved) using, for example, a mouse device. Adjusting the boundaries enables the shape and/or size of the folder tree area 413, the thumbnail area 414 and/or the file area 415 to be changed, and enables the areas to be placed in the layout desired by the user. For example, when the folder displayed in the folder tree area 413 is low in the folder hierarchy, the folder tree area 413 is required to be enlarged, but when, for example, the folder displayed in the folder tree area 413 is not low in the hierarchy, it is not necessary to enlarge the folder tree area 413. Moreover, in the case, for example, that the number of electronic files to be displayed in the thumbnail area 414 or the file area 415 is large, the thumbnail area 414 or the file area 415 is required to be enlarged, but when, for example, the number of electronic files to be displayed in the thumbnail area 414 or the file area 415 is small, it is not necessary to enlarge the thumbnail area 414 or the file area 415. Therefore, not only are the boundaries between the folder tree area 413 and the thumbnail area 414 and between the folder tree area 413 and the file area 415 freely changeable, but the boundary between the thumbnail area 414 and the file area 415 is freely changeable as well.

Thus, since the respective boundaries between the folder tree area 413, the thumbnail area 414 and the file area 415 are freely changeable, all of the electronic files stored in the designated folder may sometimes not be displayed in the thumbnail area 414. In this case, the electronic files stored in the designated folder may be displayed within the thumbnail area 414 using a scrollbar (see FIG. 11).

The thumbnail area 414 and the file area 415 are independent of each other. Therefore, an electronic file displayed in the thumbnail area 414 is not always displayed in the file area 415. For example, although the thumbnail image with the file name of "IV7I1033.jpg" is displayed in the thumbnail area 414 as shown in FIG. 11, the file name "IV7I1033.jpg" is not displayed in the file area 415. Even in this case, once an arbitrary electronic file displayed in a list in one of the thumbnail area 414 or the file area 415, for example is designated by, for example, a single click of the mouse device, the corresponding electronic file is displayed in the other area. For example, if the file "IV7I1033.jpg" were designated in the thumbnail area 414 in FIG. 11 using one mouse click, the file "IV7I1033.jpg" would also be displayed and designated in the file area 415. For example, in the thumbnail area 414 as shown in FIG. 11, the thumbnail image with the file name of "IV7I1027.jpg" is displayed, and the thumbnail image is outlined to specify that this electronic file has been designated, and in the file area 415 the file name "IV7I1027.jpg" is displayed and the file name is outlined to specify that this electronic file has been designated.

Figure 12:
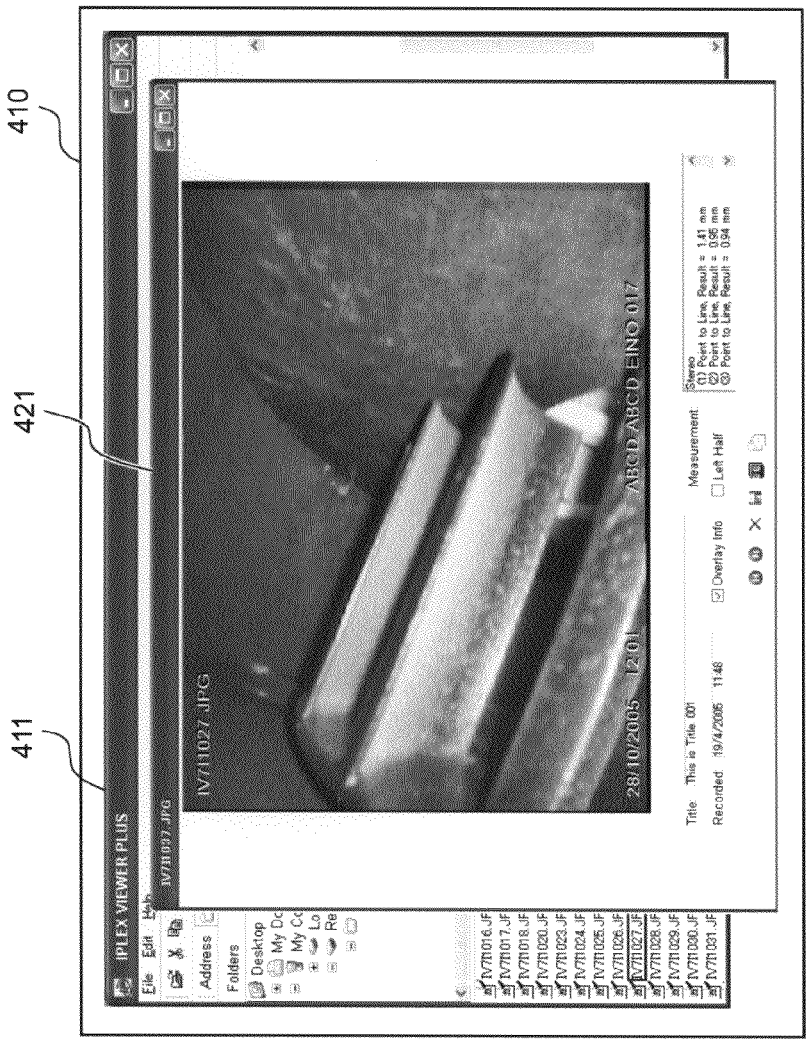
FIG. 12 illustrates displaying an image file in an image window.

In the state as shown in FIG. 11, once an arbitrary electronic file displayed in one of the thumbnail area 414 or the file area 415 is instructed to be executed, the endoscopic image viewing executes the electronic file. For example, if the thumbnail image with the file name of "IV7I1027.jpg" displayed in the thumbnail area 414 is instructed to be executed by, for example, double-clicking a mouse device, because "IV7I1027.jpg" is an electronic file of a still image, an image window 421 is opened and the still image "IV7I1027.jpg" is displayed in the image window 421, as shown in FIG. 12. The same operation is performed if the file named "IV7I1027.jpg" displayed in the file area 415 is double-clicked. That is, a user may instruct the execution of an electronic file from either the thumbnail area 414 or the file area 415, without hesitating to determine in which of the thumbnail area 414 or the file area 415 the execution should be instructed.

Figure 13:
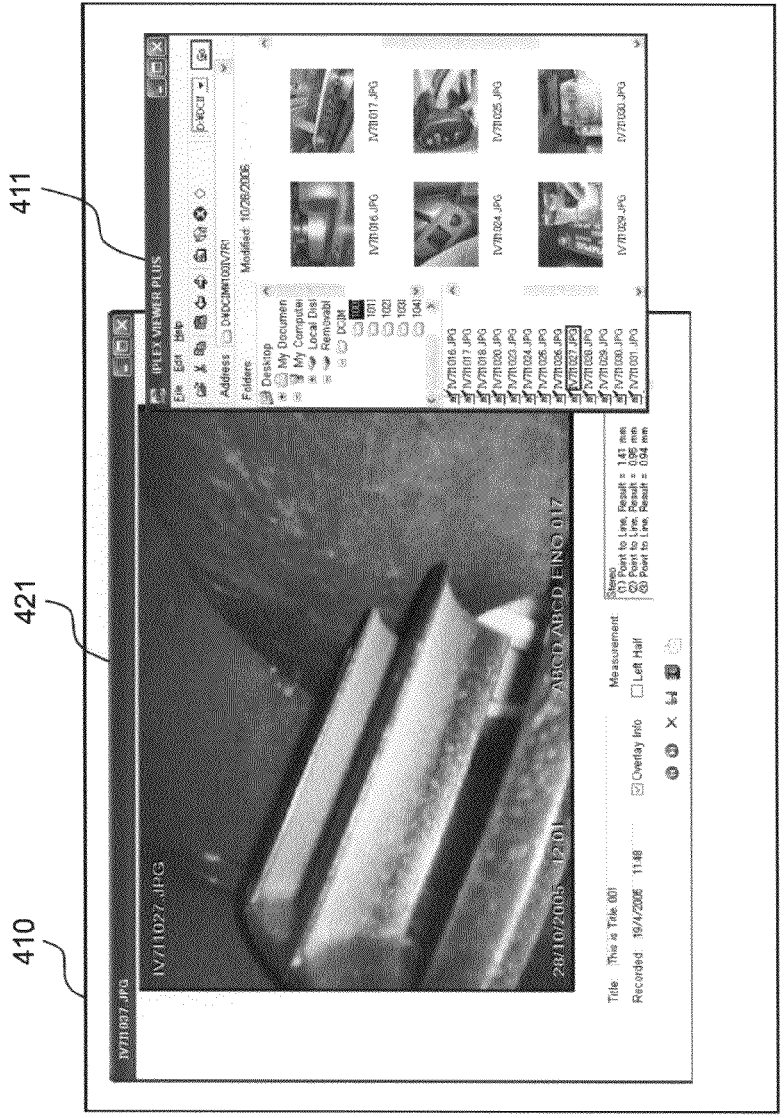
FIG. 13 illustrates displaying the image window and the main window simultaneously.

In the state as shown in FIG. 12, that is, in the display state in which the image window 421 is overlaid on the main window 411 by executing an electronic image file or the like, the user may wish to perform another operation in the main window 411. In this case, it is possible to shift the main window 411 to be overlaid on the image window 421. It is also possible to change the size of the main window 411 to be smaller, as shown in FIG. 13, which enables both the main window 411 and the image window 421 to be viewable. The main window 411 is still very convenient in use even when it is reduced in size, since the boundary between the thumbnail area 414 and the file area 415 is freely changeable.

Figure 14:
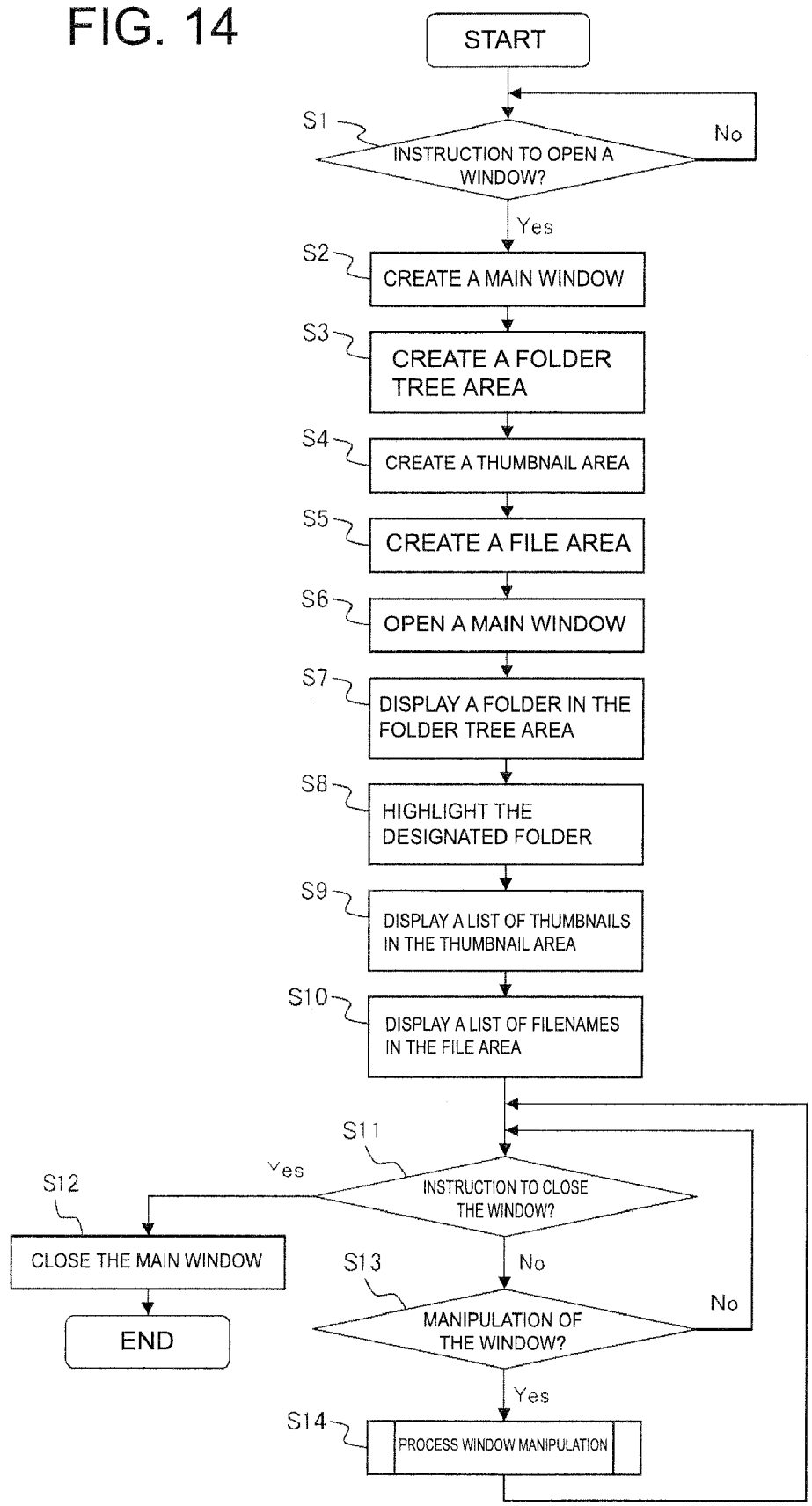
FIG. 14 illustrates a flow of information display processing when the endoscopic image viewing program is executed.
Figure 15:
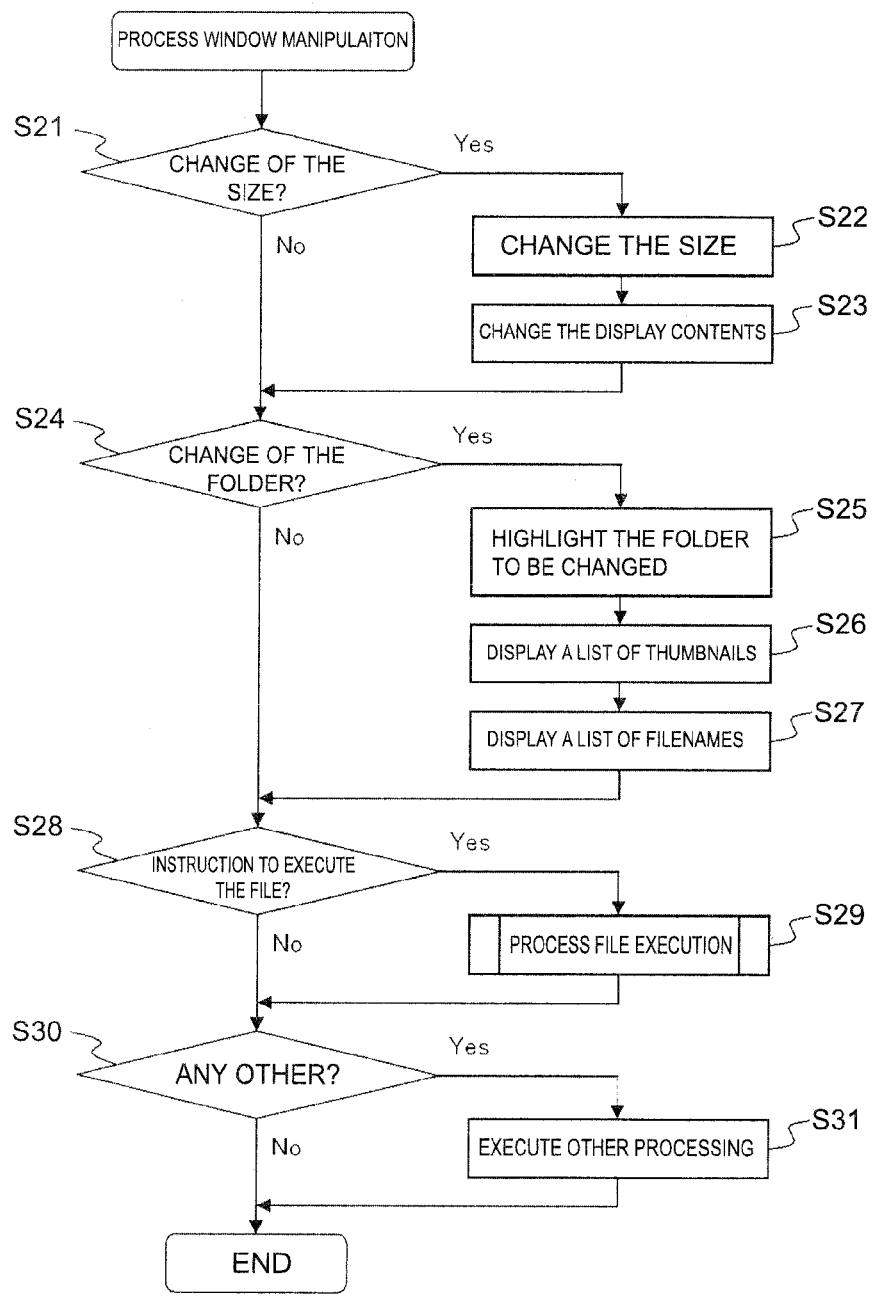
FIG. 15 illustrates a flow of a window manipulation processing sub-routine of the information display processing.
Figure 16:
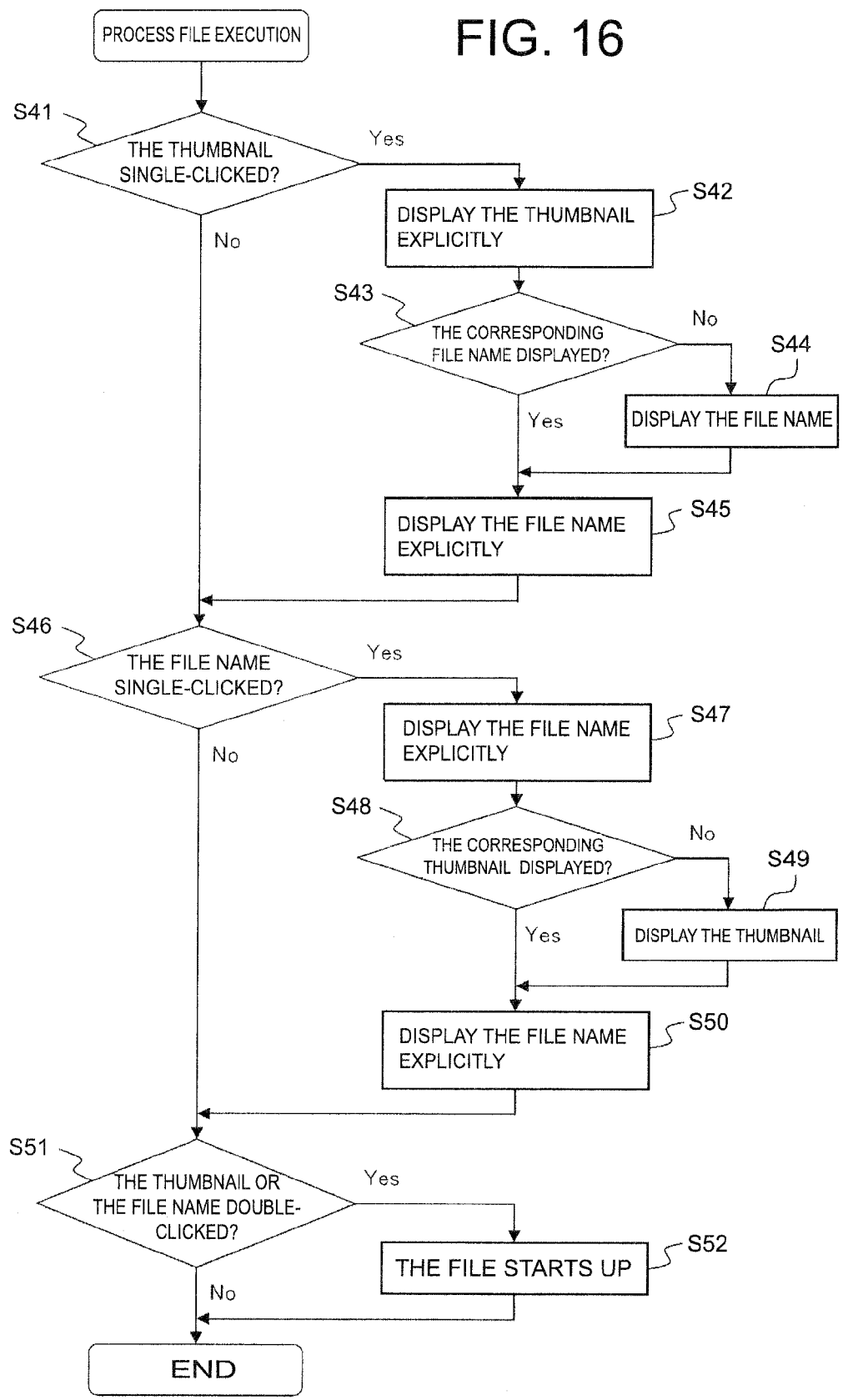
FIG. 16 illustrates a flow of a file execution processing in the window manipulation processing.

FIGS. 14-16 illustrate processes executed by the CPU 325 executing the endoscopic image viewing program 332. In particular, FIG. 14 illustrates a flow of information display processing executed by the CPU 325; FIG. 15 illustrates a flow of a window manipulation processing sub-routine of the information display processing; and FIG. 16 illustrates a flow of a file execution processing in the window manipulation processing.

First, in step S1, a judgment is made on whether there has been an instruction by a user to open a window or not. If it is judged that there has been an instruction to open the window (Yes in step S1), the main window 411 is created at step S2. On the other hand, if it is judged that there has been no instruction to open the window (No in step S1), a loop that waits for an instruction to open the window starts (the process returns to step S1). Then, in step S3, the folder tree area 413 included in the main window 411 is created; in step S4, the thumbnail area 414 included in the main window 411 is created; and in step S5, the file area 415 included in the main window 411 is created.

Subsequently, in step S6, the main window 411 including the folder tree area 413, the thumbnail area 414 and the file area 415 created in steps S2 to S5 are opened and displayed on the display screen 410 of the display 322. Next, in step S7, the hierarchically managed folders are displayed hierarchically, that is, displayed in a folder tree, in the folder tree area 413, and in step S8, a designated folder is highlighted. The typical folder designated is "My Documents" or the like, for example, as an initial value. In step S9, a list of electronic files in the designated folder displayed in the folder tree area 413 is displayed in the thumbnail format in the thumbnail area 414. If an electronic file to be displayed in the thumbnail format is not an electronic image file, an icon is displayed instead of a thumbnail image. In addition, if a list of all of the electronic files cannot be displayed within the thumbnail area 414, a scrollbar for the thumbnail area 414 is displayed and only a part of the electronic files is displayed in the list in the thumbnail area 414. In step S10, a list of the electronic files in the designated folder in the folder tree area 413 is displayed in the file name format in the file area 415. If a list of all of the electronic files cannot be displayed within the file area 415, a scrollbar for the file name area 415 is displayed and only a part of the electronic files is displayed in the list in the file name area 415.

Thus, folders are displayed hierarchically in the folder tree area 413, a list of electronic files is displayed in the thumbnail format in the thumbnail area 414, and a list of electronic files is displayed in the file name format in the file name area 415.

Next, in step S11, a judgment is made on whether there has been an instruction by a user to close the window or not. If it is judged that there has been an instruction to close the window (Yes in step S11), the main window 411 is closed in step S12. On the other hand, if it is judged that there has been no instruction to close the window (No in step S11), a judgment is made in step S13 on whether or not there has been any manipulation from a user other than an instruction to the main window 411 to close the window.

If it is judged that there has been a manipulation (Yes in step S13), in step S14, the window manipulation processing sub-routine (see FIG. 15), to execute processing in response to a manipulation from a user, is executed by the CPU 325. On the other hand, if it is judged that there has been no manipulation (No in step S13), an instruction from a user is awaited, by returning the process to step S11.

In the window manipulation processing, first, in step S21 of FIG. 15, a judgment is made on whether or not an instruction by a user is a manipulation to change the size of the main window 411 including not only changes to the size of the main window 411 itself but also changes to any of the sizes of the folder tree area 413, the thumbnail area 414 and the file area 415 included in the main window 411. For example, if the outer frame of the main window 411 is dragged using the mouse device, or if any of the boundaries between the folder tree area 413, the thumbnail area 414 and the file area 415 is dragged, it is judged to be a manipulation to change the size of the main window 411.

If the instruction is judged to be a manipulation to change the size of the main window 411 (Yes in step S21), in step S22 the size of the main window 411, the folder tree area 413, the thumbnail area 414 or the file area 415 is changed in response to the manipulation, and in step S23, the display contents of the main window 411 are changed in accordance with the size of the areas after the change. If the instructions is judged not to be a manipulation to change the size of the main window 411 in step S21 (No in step S21) or after the display contents are changed in step S23, in step S24 a judgment is made on whether the instruction by the user is a change of designation of the folder or not.

If the instructions is judged to be a change of designation of the folder (Yes in step S24), in step S25 the folder to which the designation has been changed is highlighted; in step S26 a list of electronic files in the newly designated folder is displayed in the thumbnail format in the thumbnail area 414; and in step S27 a list of electronic files in the newly designated folder is displayed in the file name format in the file area 415. In step S24, if the instruction is judged not to be a change of designation of the folder (No in step S24), or after the list display is performed in step S27, in step S28, a judgment is made on whether or not the instruction by a user is an instruction to execute an electronic file.

If the instruction is judged to be an instruction to execute the electronic file (Yes in step S28), in step S29, the sub-routine "file execution processing", which will be described with respect to FIG. 16, is executed. Thereafter, or if it is judged in step S28 that the instruction is not an instruction to execute an electronic file (No in step S28), in step S30, a judgment is made on whether or not the instruction by the user is another manipulation, other than a manipulation to close the main window 411, to change the size of the main window 411, to change the designated folder, or to execute an electronic file. If the instruction is judged to be another manipulation (Yes in step S30), in step S31, the other processing is executed in accordance with the other manipulation, and the process returns to step S11. And if the instruction is judged not to be even the other manipulation (No in step S31), an instruction from a user will be awaited, after the process returns to step S11.

In the file execution processing, first, in step S41 of FIG. 16, a judgment is made on whether or not the instruction by the user is predetermined manipulation (for example, in this case a single click using the mouse device) to an electronic file displayed in a list in the thumbnail format in the thumbnail area 414. If the instruction is judged to be the single click (Yes in step S41), in step S42, the electronic file which has been single-clicked (the thumbnail image) is highlighted by, for example, outlining the electronic file with a rectangle. Then, in step S43, a judgment is made on whether a file name corresponding to the single-clicked electronic file is displayed in the file area 415 or not. If it is judged that the file name is not displayed (No in step S43), in step S44, the inside of the file area 415 is scrolled, or the like, so that the corresponding file name is displayed. On the other hand, if it is judged that the file name is displayed (Yes in step S43), or after the corresponding file name is displayed in step S45, the corresponding file name is highlighted by, for example, outlining the file name with a rectangle.

Then, after the file name is highlighted in step S45, or if the instruction is judged not to be the single-click manipulation of the thumbnail image in step S41 (No in step S41), in step S46, a judgment is made on whether or not the instruction by the user is a predetermined manipulation (for example, in this case a single click using the mouse device) to an electronic file displayed in a list in the file name format in the file area 415. If the instruction is judged to be the single-click manipulation (Yes in step S46), in step S47, the single-clicked electronic file (the file name) is highlighted by, for example, outlining the file name with a rectangle. And, in step S48, a judgment is made on whether the thumbnail image corresponding to the single-clicked electronic file is displayed in the thumbnail area 414 or not. If it is judged that the thumbnail image is not displayed (No in step S48), in step S49, the thumbnail area 414 is scrolled, or the like, so that the corresponding thumbnail image is be displayed. On the other hand, if it is judged that the thumbnail image is displayed (Yes in step S48), or after the corresponding thumbnail image is displayed in step S49, in step S50 the corresponding thumbnail image is highlighted by, for example, outlining the thumbnail image with a rectangle.

Then, after the thumbnail image is highlighted in step S50, or if the instruction is judged not to be the manipulation of single-clicking the file name in step S46 (No in step S46), in step S51 a judgment is made on whether or the instruction by the user is a predetermined manipulation (for example, in this case a double click using the mouse device) to an electronic file displayed in a list in the thumbnail format in the thumbnail area 414 or to an electronic file displayed in a list in the file name format in the file area 415.

If the instruction is judged to be the double-click manipulation (Yes in step S51), in step S52 the double-clicked electronic file is executed. For example, if the electronic file is a still image, the still image is displayed; if the electronic file is a moving image, the moving image is reproduced; or if the electronic file is an audio file, the audio file is reproduced. And, after the electronic file is executed in step S52, or if the instruction is judged not to be the double-click manipulation (No in step S51), then the process returns to step S30 in FIG. 15 as described above.

Figure 17:
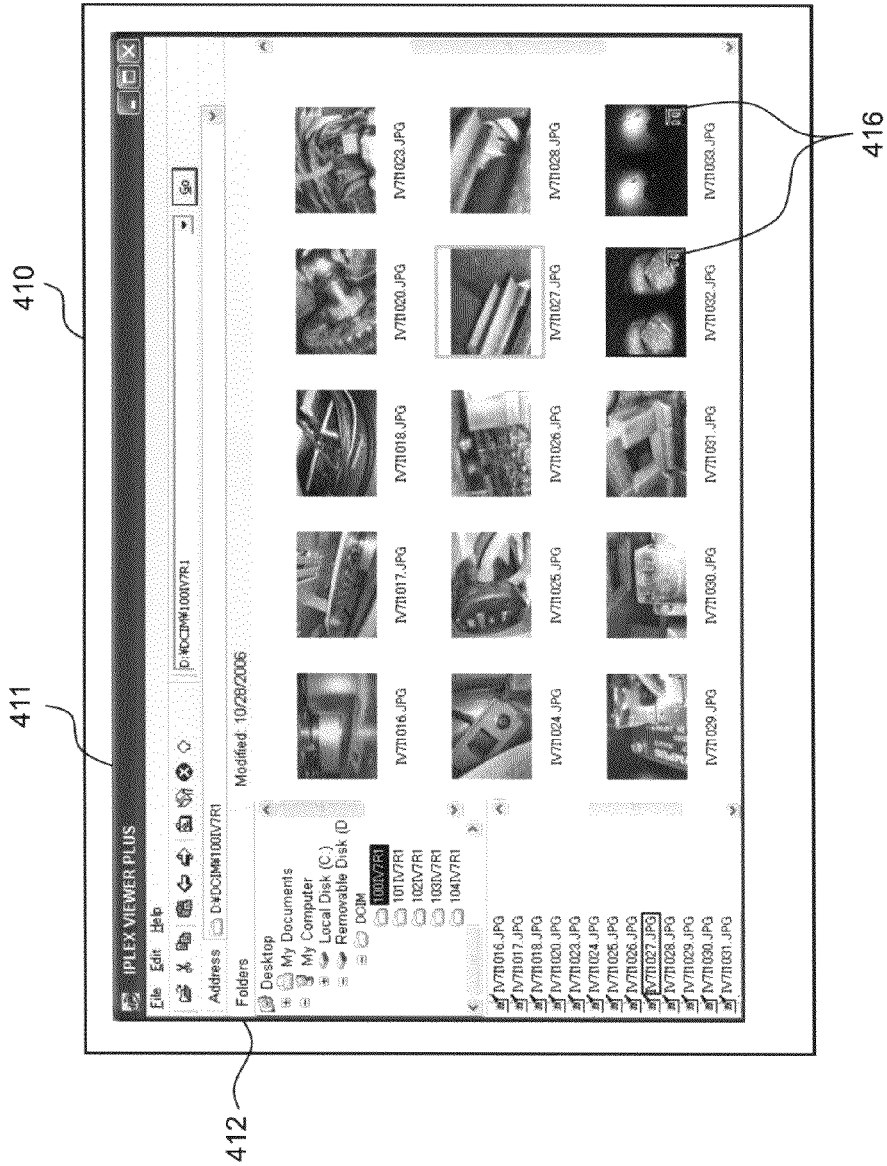
FIG. 17 illustrates additional features of the display performed in the main window when executing the endoscopic image viewing program.

As shown in FIG. 17, a date (or date and time) indicating a time at which a currently designated folder or file was last modified may be displayed in toolbar 412 (or one of a plurality of toolbars 412; the toolbar under the address bar in FIG. 17 can be considered another kind of toolbar). See the displayed information "Modified: Oct. 28, 2006" in FIG. 17. If no electronic file is designated, then the date (or date and time) corresponding to the designated folder is displayed. If an electronic file is designated, then the date (or date and time) corresponding to the designated electronic file is displayed.

If the electronic file displayed in the thumbnail area 414 is a moving image file, the thumbnail image that is displayed for the electronic moving image file is a reduced image of the first frame of the electronic moving image file. As described above, double-clicking on the thumbnail image or the file name causes an animation (moving image) to be reproduced when the double-clicked electronic file is an electronic moving image file. Moreover, if the electronic file displayed in the thumbnail area 414 is an electronic image file that has been stereoscopically measured by an endoscopic device, a measurement icon 416 is displayed at, for example, the vicinity of the bottom right corner of the thumbnail image. Thereby, the user can easily find any electronic image file having a stereoscopically measured result. In addition, if the electronic file displayed in the thumbnail area 414 is not an electronic image file, a predetermined icon is displayed instead of a thumbnail image. If the icon is double-clicked, the same software that is activated by double-clicking a file name is activated, thereby reproducing the electronic file. For example, if the electronic file is an electronic audio file, an icon indicating the electronic audio file is displayed and double-clicking causes software for reproducing the electronic audio file to be activated and the audio data in the electronic audio file to be reproduced. Still further, if an electronic still image file has the same file name as an electronic audio file, when the electronic audio file is reproduced, the electronic still image file is simultaneously displayed in the image window 421. For example, if the electronic still image file "IV7I0030.JPG" and the electronic audio file "IV7I0030.WAV" with the same name as the electronic image file are present in the same folder, reproduction of the electronic audio file "IV7I0030.WAV" causes the image window 421 to be opened and the electronic still image file "IV7I0030.JPG" is displayed.

Moreover, although it has been described above that when an image file is executed the image is displayed in a new window (image window 421), the image may instead be displayed in the thumbnail area 414, in place of the list of thumbnail images.

FIGS. 18-26 illustrate processes performed when one or more electronic image files are executed from the main window 411 to be displayed, when the endoscopic image viewing program 332 is executed by the personal computer 320 (by the CPU 325 of the personal computer 320).

Figure 18:
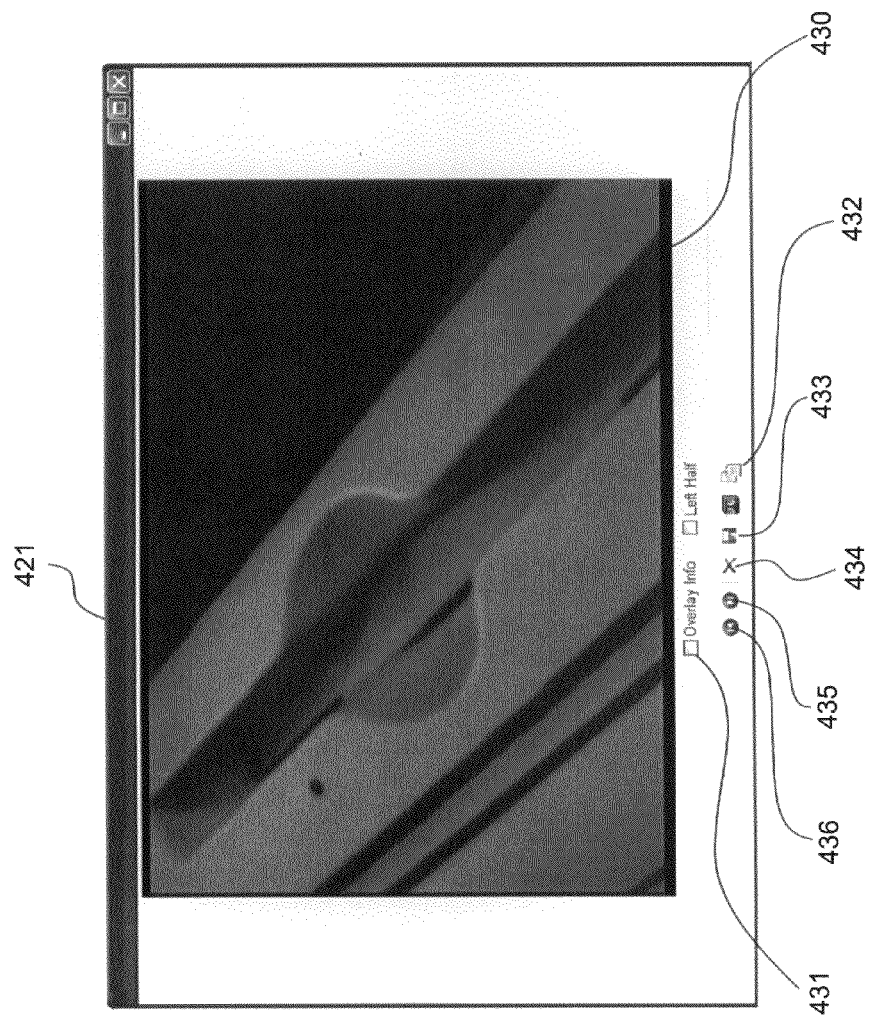
FIG. 18 illustrates displaying an endoscopic image in an image window.
Figure 19:
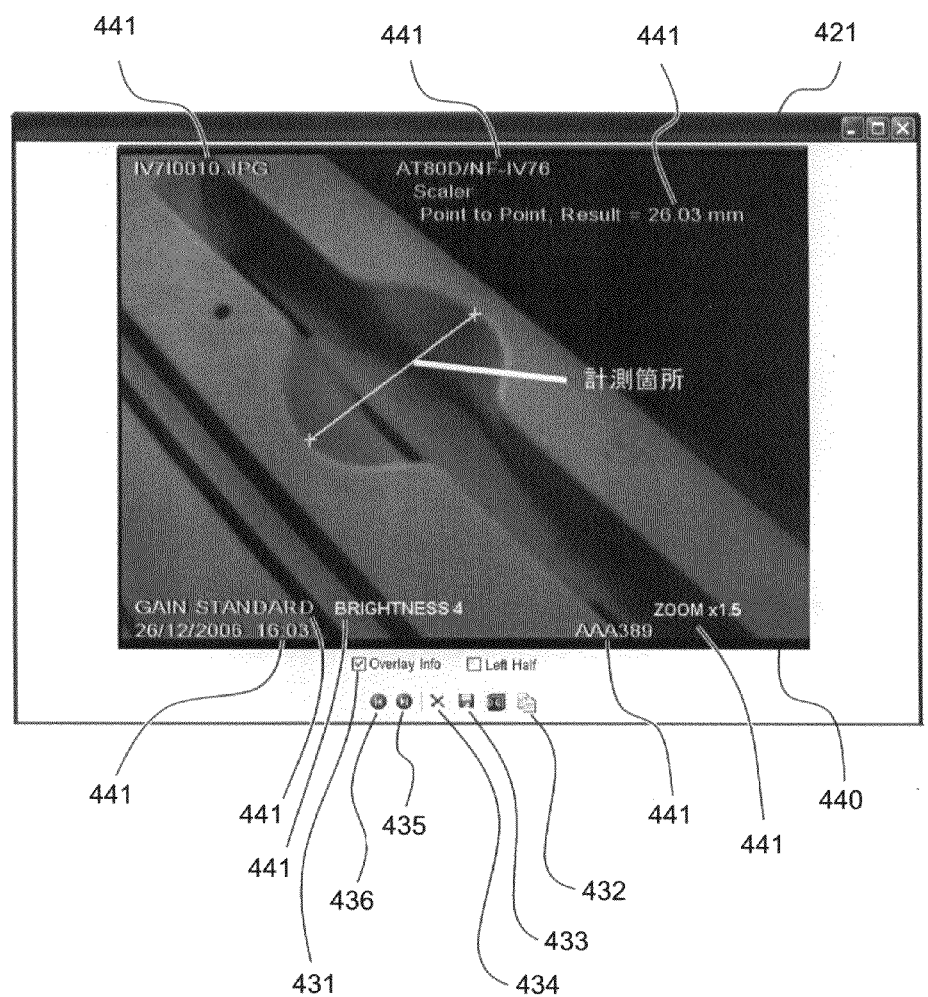
FIG. 19 illustrates displaying an overlay image, which includes an endoscopic image and overlay information, in an image window.

FIG. 18 illustrates an endoscopic image which is displayed in an image window 421 by being executed from the main window 411 (e.g., by double-clicked in the list in the thumbnail area 414 or the file area 415) as described above. FIG. 19 illustrates the display of an overlay image, which is an image in which overlay information is overlaid on the endoscopic image in the image window 421. When an electronic file such as an endoscopic image is instructed to be executed, the endoscopic image 430 is typically displayed only as shown in FIG. 18. However, with the endoscopic image viewing program 332, it is also possible to display an overlay image, which is the endoscopic image 430 with various overlay information 441 relating to the endoscopic image 430 overlaid on the endoscopic image 430 as shown in FIG. 19.

While various incidental information incidental to the endoscopic image recorded on a recording medium (e.g., memory card 311) is recorded on the recording medium together with the endoscopic image in compliance with a standard such as Exif, an image format standardized by JEIDA (Japan Electronic Industry Development Association), as shown in FIG. 18, if an overlay ("Overlay Info") checkbox 431 is not selected, that is, is not checked, the only endoscopic image 430 is displayed in the image window 421. On the other hand, if the overlay checkbox 431 is checked, the overlay image 440 is displayed as shown in FIG. 19. The overlay image 440 includes various overlay information 441 such as a file name, a name of an optical adapter used at the distal end of an endoscope to capture the endoscopic image, a length measurement result, a date and time of image recording, and the like. The overlay checkbox 431 may be checked or unchecked by a selection or deselection operation, such as, for example, clicking with the mouse device.

Also, by clicking a copy icon 432 using the mouse device, or the like, if the endoscopic image 430 is displayed as shown in FIG. 18, the endoscopic image 430 is copied in the buffer memory of the personal computer 320, and if the overlay image 440 is displayed as shown in FIG. 19, the overlay image is copied in the buffer memory. Then, the endoscopic image 430 or the overlay image 440 may be utilized with another application program such as word processing software or with another device, or the like.

By clicking a storage icon 433 using the mouse device, or the like, if the endoscopic image 430 is displayed as shown in FIG. 18, the endoscopic image 430 is stored in a recording medium (for example, the hard disk 321, or the portable/removable recording medium 311), and if the overlay image 440 is displayed on the endoscopic image as shown in FIG. 19, the overlay image 440 is stored in the recording medium. Then, the endoscopic image 430 or the overlay image 440 stored in the recording medium may be utilized as an electronic file with another application program such as mailer software or with a device, or the like.

By clicking a deletion icon 434 using the mouse device, or the like, the endoscopic image 430 is deleted, and the image display in the image window 421 disappears.

By clicking a forward icon 435 using the mouse device, or the like, if the endoscopic image 430 is displayed as shown in FIG. 19, the next endoscopic image 430 (the endoscopic image stored immediately after the currently displayed endoscopic image in the same folder) is displayed in the image window 421, and if the overlay image 440 is displayed as shown in FIG. 19, the next overlay image 440 (the endoscopic image stored immediately after the currently displayed endoscopic image in the same folder, along with the corresponding overlay information) is displayed in the image window 421.

By clicking a backward icon 436 using the mouse device, or the like, if the endoscopic image 430 is displayed as shown in FIG. 18, the previous endoscopic image 430 (the endoscopic image stored immediately before the currently displayed endoscopic image in the same folder) is displayed in the image window 421, and if the overlay image 440 is displayed as shown in FIG. 18, the previous overlay image 440 (the endoscopic image stored immediately before the currently displayed endoscopic image in the same folder, along with the corresponding overlay information) is displayed in the image window 421.

Figure 20:
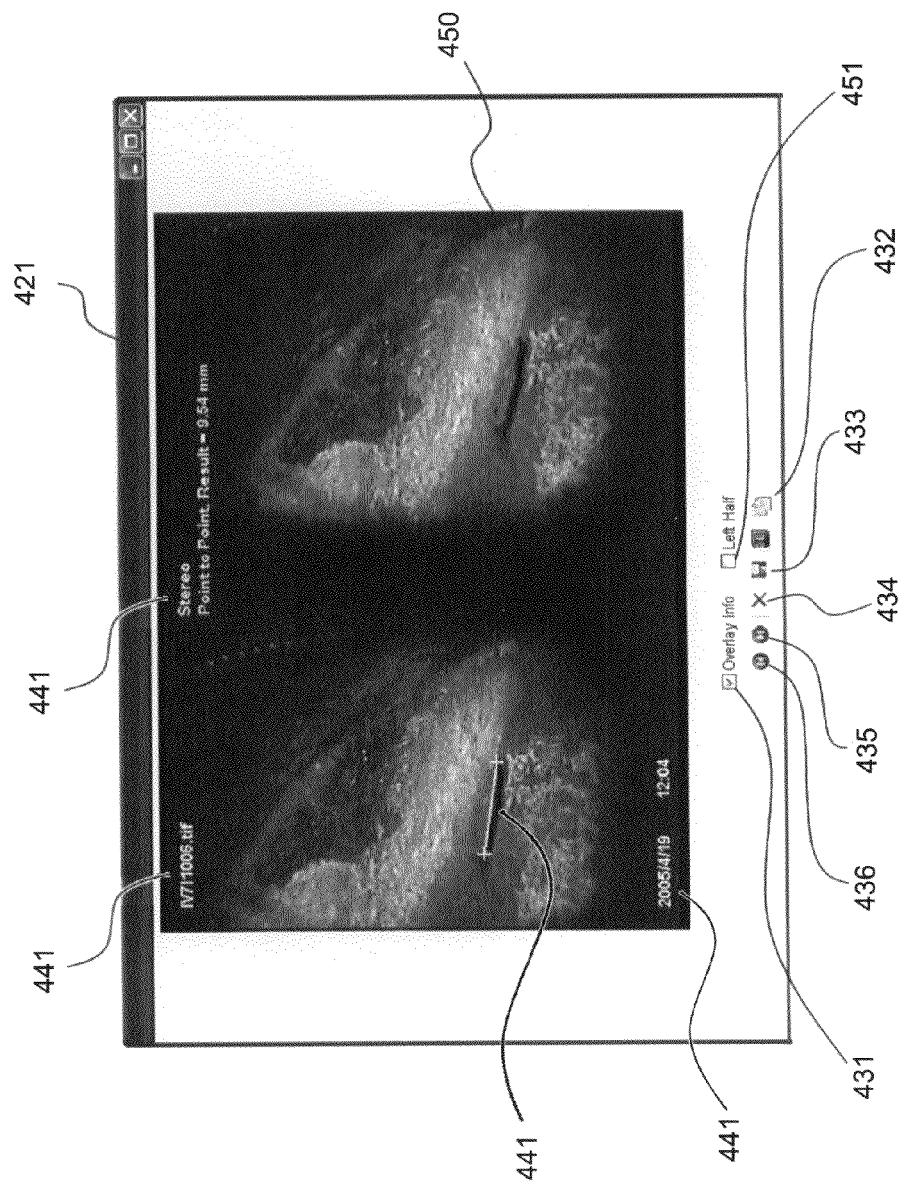
FIG. 20 illustrates displaying a stereoscopic image in an image window.
Figure 21:
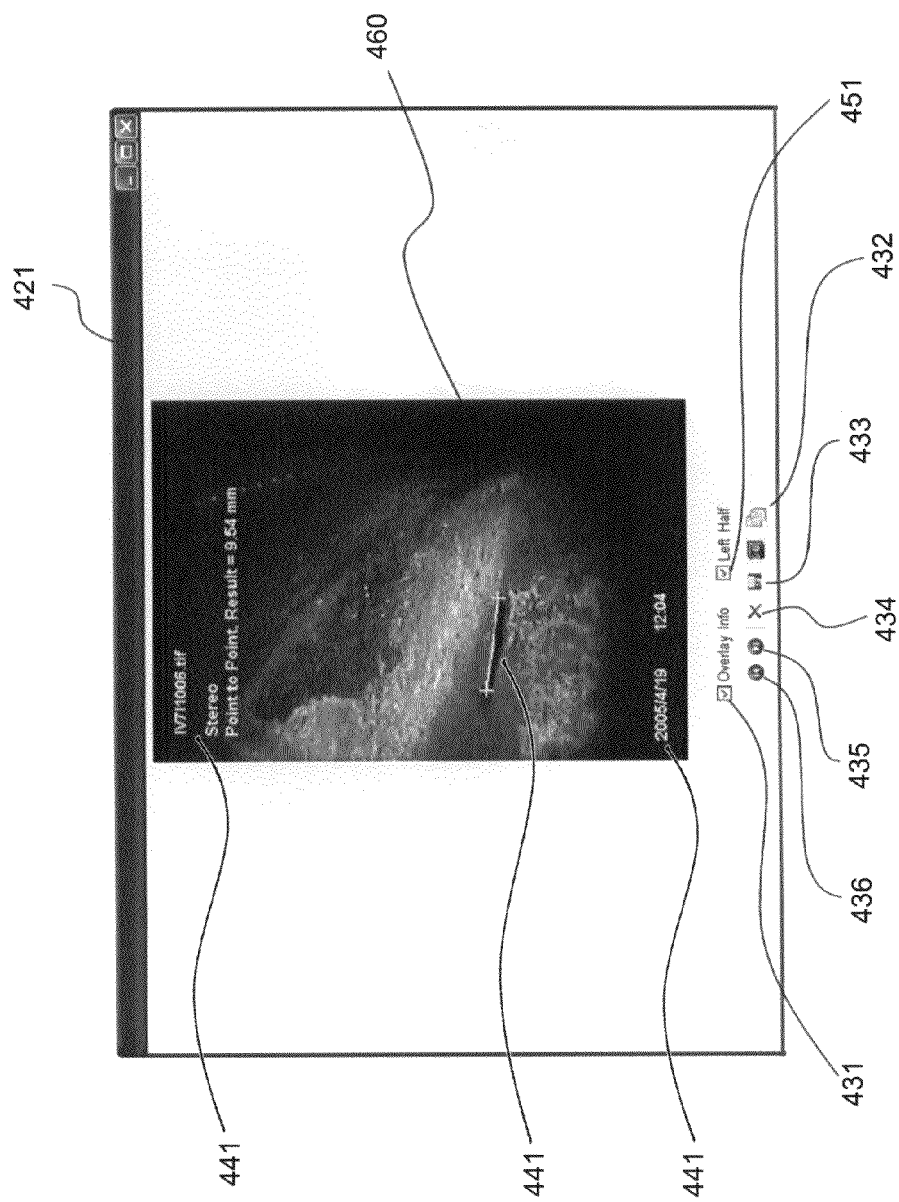
FIG. 21 illustrates displaying a half image of a stereoscopic image in an image window.

FIG. 20 illustrates displaying a stereoscopically measured image, and FIG. 21 illustrates displaying a half image of the stereoscopically measured image. If the electronic file that is executed from the main window 411 to be displayed in the image window 421 is a stereoscopically measured image 450 taken stereoscopically, the stereoscopically measured image 450 is typically displayed only as shown in FIG. 20. However, with the endoscopic image viewing program 332 it is also possible to display a half image 460, which is an image of the left half or the right half of the stereoscopically measured image 450. Switchover between the display of the stereoscopically measured image 450 and the display of the half image 460 may be performed by selecting, that is, by checking, a half checkbox 451 ("Left Half" checkbox in FIGS. 20 and 21). That is, if the half checkbox 451 is not checked, the stereoscopically measured image 450 is displayed in the image window 421 as shown in FIG. 20. On the other hand, if the half checkbox 451 is checked, the half image 460 is displayed as shown in FIG. 21. In the example shown in FIGS. 20 and 21, a checkbox is provided to cause display of only the left half image 460. The checkbox may instead be provided to cause display of only the right half image. And the endoscopic image viewing program 332 may alternatively enable the user to arbitrarily select which one of the left and right half images is to be displayed as the half image 460 (for example, by providing both a "Left Half" checkbox and a "Right Half" checkbox").

It is also possible with the endoscopic image viewing program 332 to display overlay information 441 on the stereoscopically measured image 450, and to display overlay information on the half image 460, by checking the overlay checkbox 431.

The overlay information 441 displayed on the stereoscopically measured image 450 and on the half image 460 may be the same, as shown in FIGS. 20 and 21, although the position of the overlay information 441 is changed when the stereoscopically measured image 450 is reduced to the half image 460, as shown in FIGS. 20 and 21. More specifically, the display position of the overlay image is aligned in accordance with the selection of which manner of displaying the stereoscopically measured image is selected. When the entire stereoscopically measured image 450 is displayed, the overlay information 441 is displayed over both the left and right half images as shown in FIG. 20. On the other hand, when the half image 460 is displayed, the display positions of the overlay information 441 are adjusted so that the overlay information 441 is completely located within the half image 460, as shown in FIG. 21.

Alternatively, all of the overlay information 441 is not necessarily displayed when only the half image 460 is displayed. It is possible to display only a part of the overlay information 441 on the half image 460 when the half image 460 is displayed alone. In more detail, the overlay information 441 may, for example, be divided into information designated as high priority information, and information designated as low priority information. In this case, when the stereoscopically measured image 450 is displayed, all of the overlay information (both low and high priority) is displayed. On the other hand when the half image is displayed, only the high priority overlay information is displayed.

Figure 27:
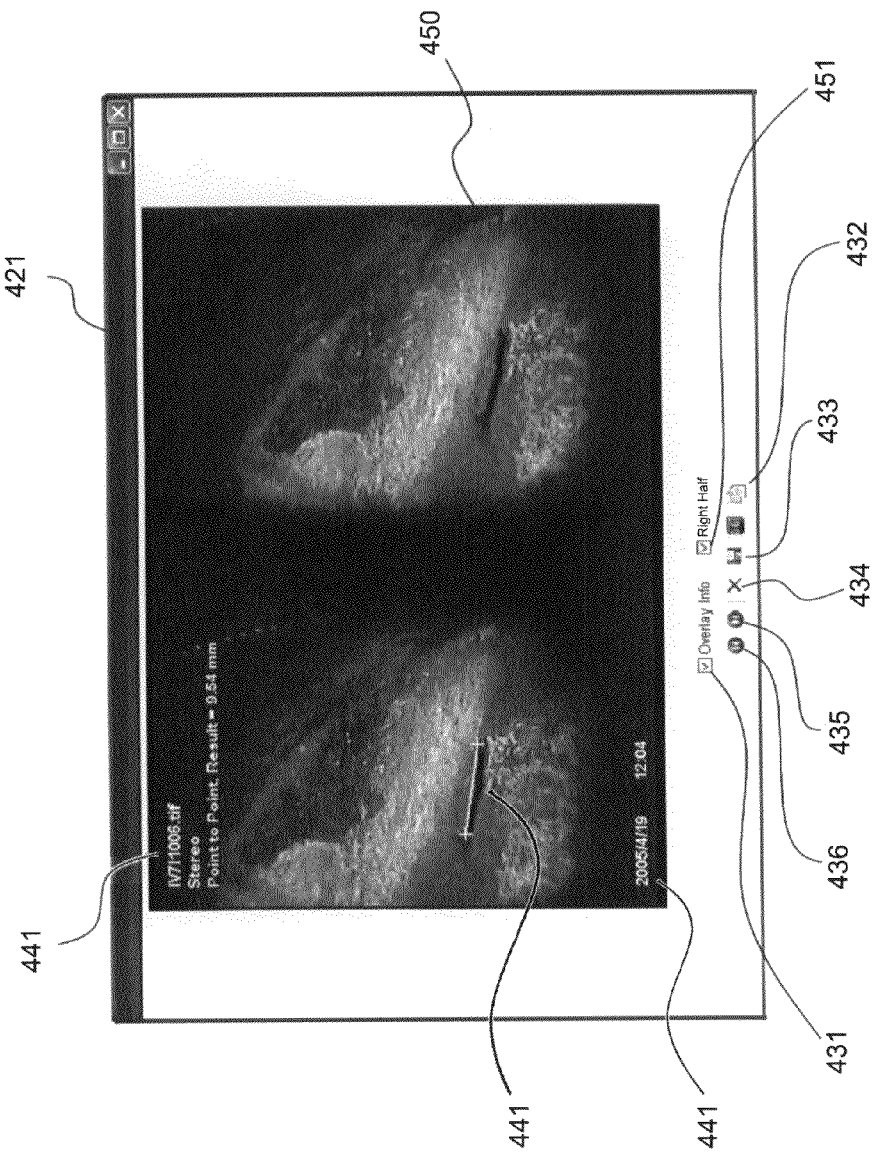
FIG. 27 illustrates an alternative technique for selecting one of two displayed half images of a stereoscopically measured image.

Still further, accordingly to one aspect of the present invention, the left and right half images in the stereoscopically measured image 450 may be independently selectable. That is, one or the other of the left and right half images may be selected while both of the left and right half images continue to be displayed, and the positions at which the overlay information is displayed may be changed in accordance with which one, if any, of the left and right images is selected. The selection may be performed, for example, using the half checkbox 451, or by selecting one of the left and right half images by clicking on the half image using the mouse device of the personal computer 320. For example, if, while the stereoscopically measured image 450 is displayed, the right image is selected as shown in FIG. 27, the overlay information 441 may be repositioned to be overlaid only on the left half image, so that the right half image can be viewed without information overlaid thereon.

Figure 28:
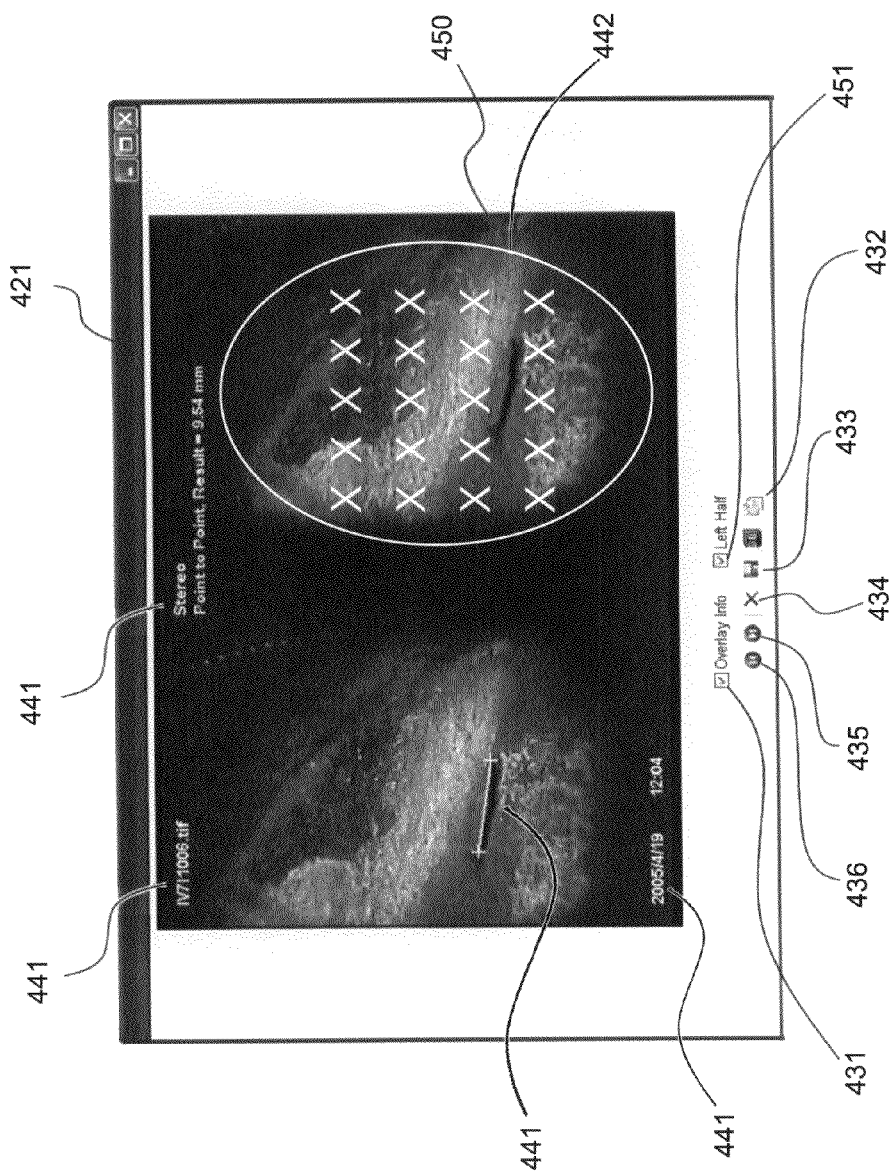
FIG. 28 illustrates displaying additional overlay information when one of two displayed half images of a stereoscopically measured image is selected.

Additionally, or alternatively, when the left half image (for example) is selected, additional overlay information 442 may be overlaid on the right half image as shown in FIG. 28. This additional overlay information 442 (indicates by X's in FIG. 28) is, for example, information that is not displayed when the whole stereoscopically measured image 450 is selected (when neither the left or right half images is selected). And this additional overlay information may be, for example, information that is of a lower priority still (i.e., of a lower priority than the high and low priority information mentioned above).

Moreover, according to another aspect of the present invention, the positions at which the overlay information 441 is displayed differ depending on whether a single image or multiple images are displayed. When two images (for example, left and right half images of the stereoscopically measured image, or two independent images) are displayed simultaneously, the overlay information corresponding to the images is displayed over a wider area corresponding to the two images. On the other hand, when only a single image is displayed (for example, the half image 460, or another single image), the overlay information 441 corresponding to the image is displayed in a narrower area corresponding to the single image. Thus, when the display performed using the endoscopic image viewing program 332 is changed, for any reason (for example, due to changing from displaying the stereoscopically measured image 450 to the half image 460, or for another reason) from displaying one image to displaying two images, or from displaying two images to displaying one image, the positions at which the overlay information 441 is displayed change. Accordingly, when two images (or two half images) are displayed together, the corresponding overlay information 441 is displayed at first predetermined positions, and if one image (or one half image) is displayed, the corresponding overlay information 441 is displayed at second predetermined positions, in a narrower area than the first predetermined positions.

Figure 22:
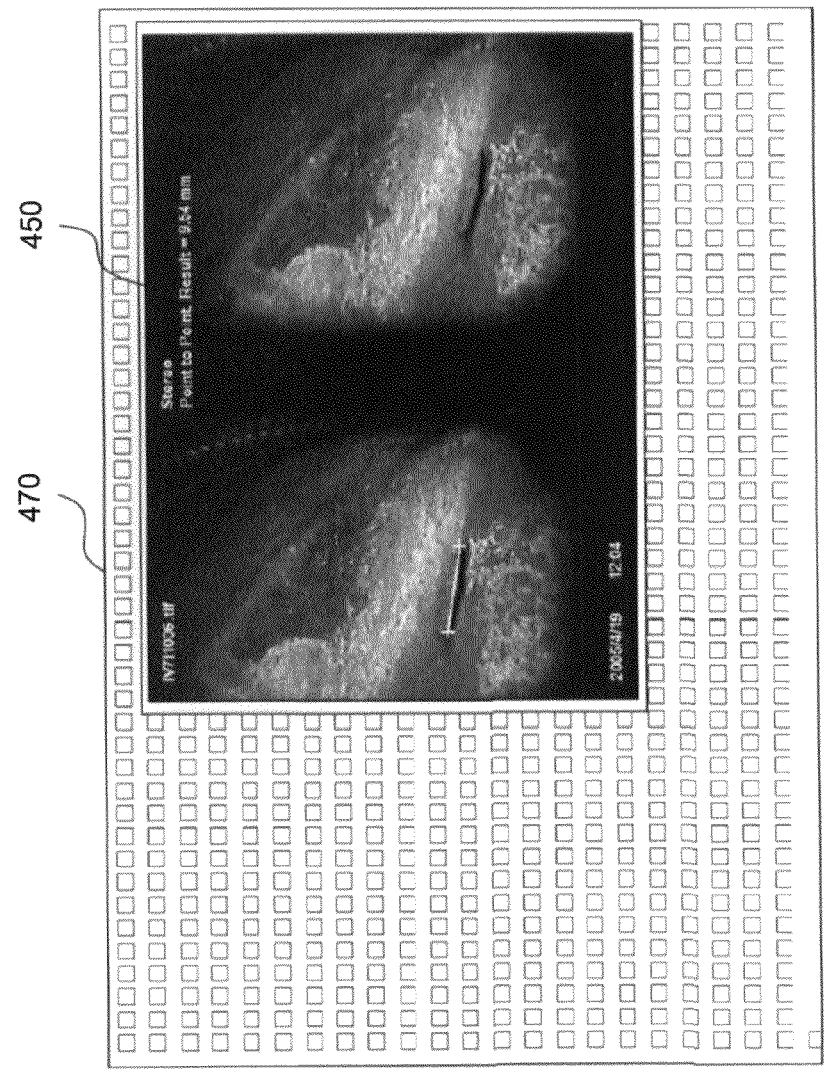
FIG. 22 illustrates a stereoscopically measured image attached to a manuscript of another application.
Figure 23:
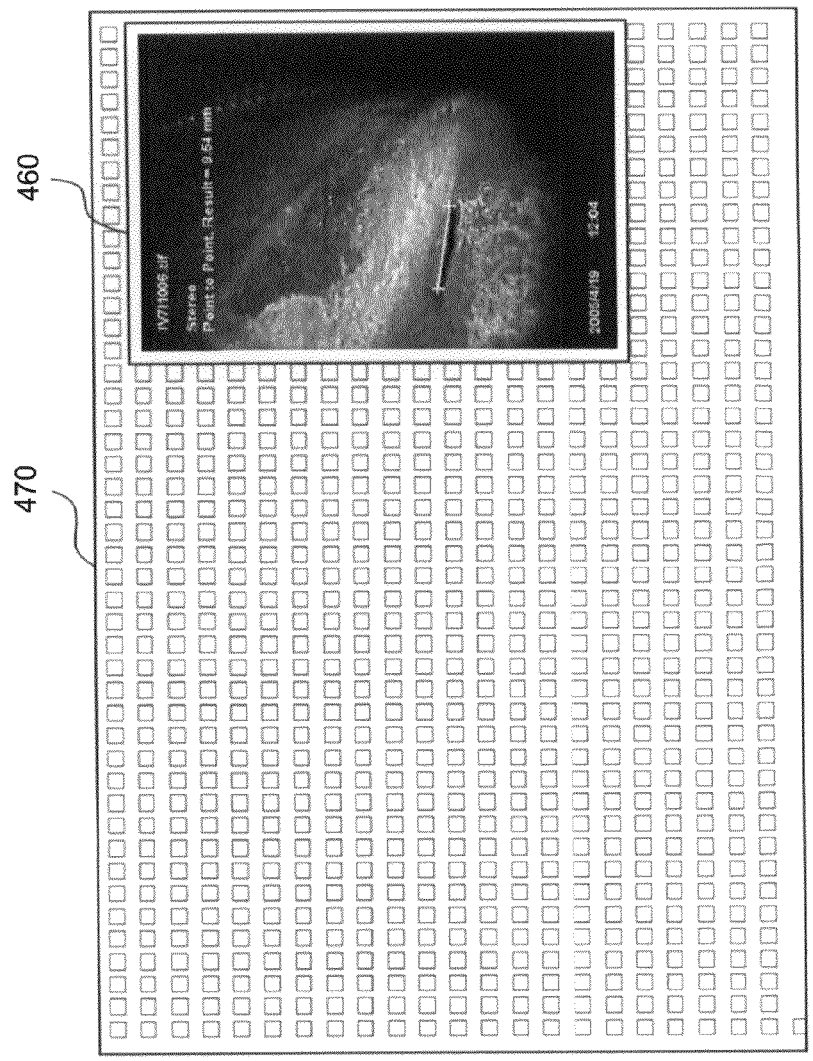
FIG. 23 illustrates a half image of a stereoscopically measured image in a manuscript of another application.

By clicking the copy icon 432 using the mouse device, or the like, if the stereoscopically measured image 450 is displayed as shown in FIG. 20, the stereoscopically measured image 450 is copied in the buffer memory, and if the half image 460 is displayed as shown in FIG. 21, the half image 460 is copied in the buffer memory. Then, the stereoscopically measured image 450 or the half image 460 copied in the buffer memory may be utilized with another application program such as word processing software or with another device, or the like. FIG. 22 illustrates an example of the stereoscopically measured image 450 attached to a manuscript 470 of another application, and FIG. 23 illustrates an example of the half image 460 attached to a manuscript 470 of another application. As can be seen in FIGS. 22 and 23, the half image 460 requires half of the space in the manuscript 470 as is required by the stereoscopically measured image 450.

By clicking the storage icon 433 using the mouse device, or the like, the stereoscopically measured image 450 or the half image 460 is stored in the recording medium (such as the hard disk 321 or the portable/removable recording medium 311). Then, the stereoscopically measured image 450 or the half image 460 stored in the recording medium may be utilized as an electronic file with another application program such as mailer software or with another device, or the like.

By clicking the deletion icon 434 using the mouse device, or the like, the stereoscopically measured image 450 is deleted (whether the stereoscopically measured image 450 or the half image 460 is displayed) and the image display in the image window 421 disappears.

By clicking the forward icon 435 using the mouse device, or the like, the image is switched to the next image, for example a stereoscopically measured image 450 or the corresponding half image 460 (if the checkbox 451 is checked), which is stored immediately after the currently displayed image in the same folder. And by clicking the backward icon 436 using the mouse device, or the like, the image is switched to the previous image, for example a stereoscopically measured image 450 or the corresponding half image 460 (if the checkbox 451 is checked), which is stored immediately before the currently displayed image in the same folder.

Moreover, with the endoscopic image viewing program 332, a plurality of images can be displayed side by side, and the displayed images may be overlay images. More specifically, by instructing a plurality of electronic image files to be executed from the main window 411 at the same time, for example, the user can instruct the endoscopic image viewing program 332 to simultaneously display the plurality of images in the image window 421. The endoscopic image viewing program 332 displays the images, each of which may be, for example, an endoscopic image, an overlay image, a stereoscopically measured image, and/or a half image, simultaneously (e.g., side by side) without reducing the size of the images.

Figure 24:
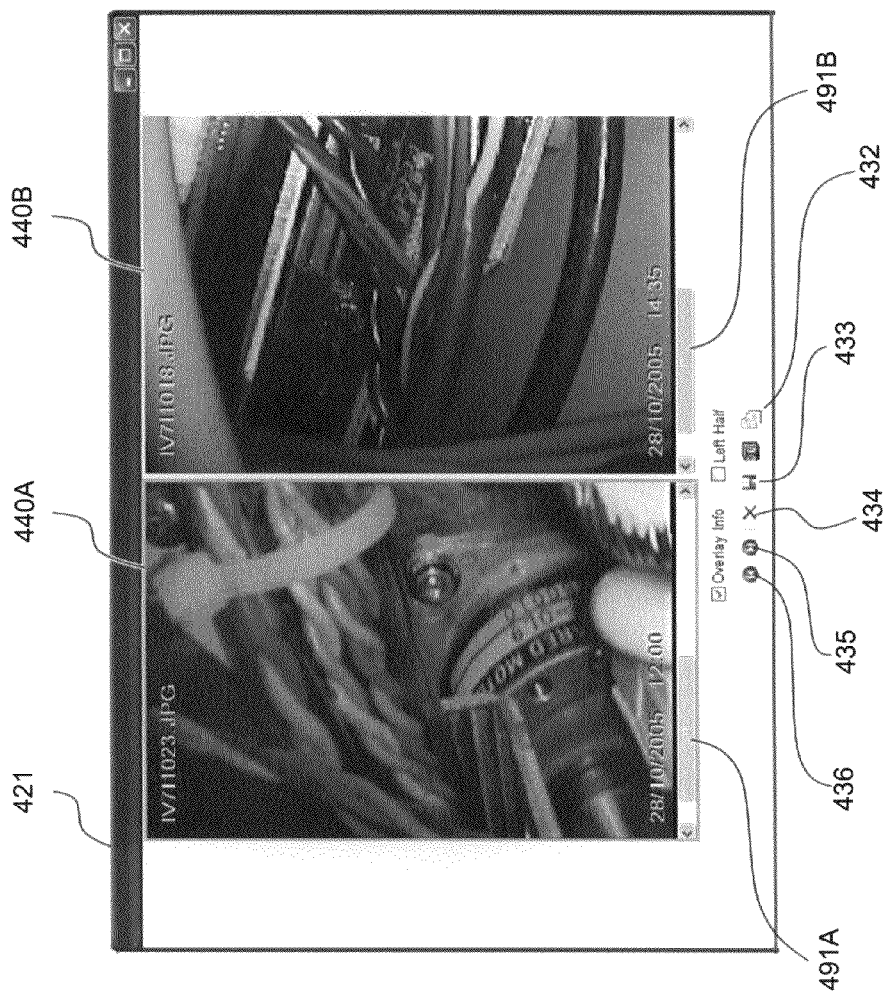
FIG. 24 illustrates displaying two images side by side without any reduction in image size.

FIG. 24 illustrates two overlay images 440A and 440B which are displayed side by side without any reduction in size. However, because the image window 421 is too small to display both of the overlay images 440A and 440B entirely, scrolling is made possible using scrollbars 491A and 491B corresponding to the images 440A and 440B, respectively.

The scrollbars 491A and 491B may be provided to operate independently of each other (such that scrolling one image does not cause scrolling of the other image). Alternatively, the scrollbars 491A and 491B may be synchronized with each other (such that scrolling of one image causes simultaneous scrolling of the other image). Moreover, instead of two scroll bars 491A and 491B, a single scroll bar may be provided which causes the images to scroll simultaneously in accordance with operation of the one scrollbar.

When scrolling an overlay image (e.g., one of the overlay images 440A and 440B) according to one aspect of the present invention, all of the overlay information 441 is scrolled along with the image on which the overlay information 441 is provided. Preferably, however, only a portion of the overlay information 441 is scrolled along with the image on which the overlay information 441 is provided. That is, preferably, the overlay information 441 is divided into a first portion that is scrolled with the image, and a second portion that is not scrolled with the image. The first portion of the overlay information 441 is information that is related to a specific portion or portions of the image. For example, the first portion of the overlay information 441 may include an indication of one or more points and/or lines connecting such points with respect to which a distance or area has been measured stereoscopically. The second portion of the overlay information 441 is not related to a specific portion of the image. For example, the second portion of the overlay information 441 may include a date and time at which the image was taken and a measurement result of stereoscopic measurement.

Figure 25:
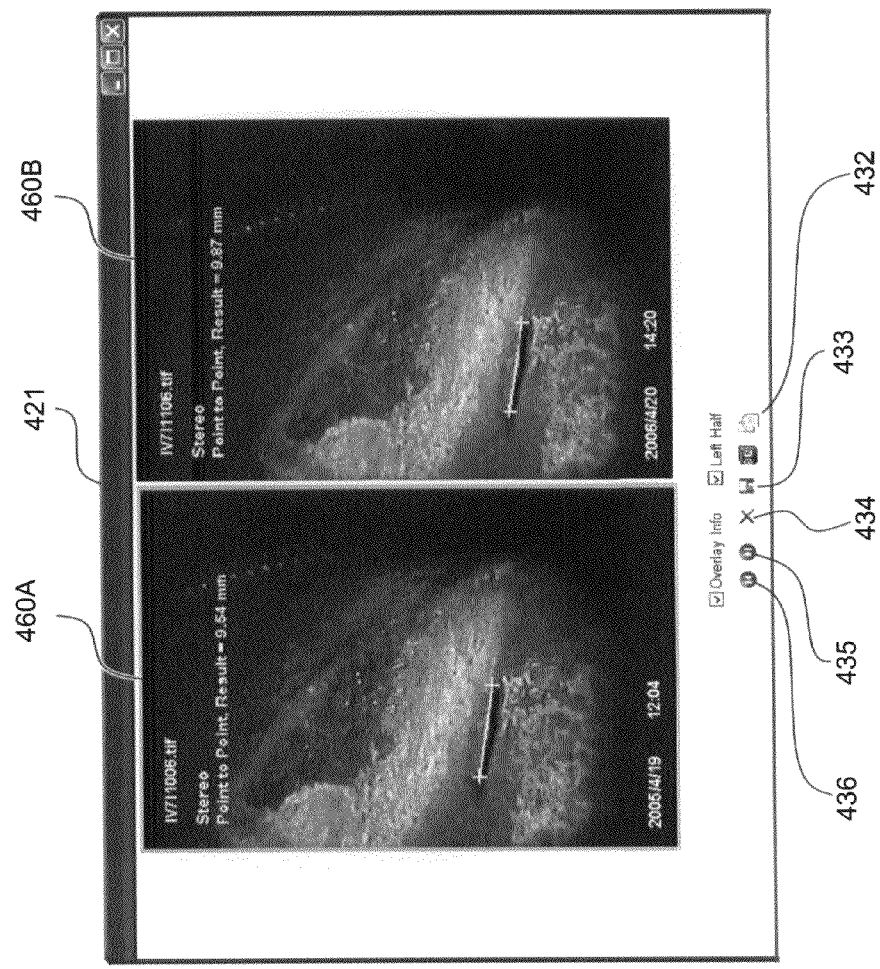
FIG. 25 illustrates displaying two half images of stereoscopically measured images side by side without any reduction in size.

FIG. 25 illustrates two half images 460A and 460B displayed side by side without any reduction in size. Because displaying of these half images 460A and 460B side by side in the image window 421 is possible, it is not necessary to use the scrollbars 491A and 491B as shown in FIG. 24.

Copying, storage and deletion of images, as well as switching between images in the same folder is possible by clicking the copy icon 432, the storage icon 433, the deletion icon 434, the forward icon 435 or the backward icon 436 even when a plurality of images are displayed as shown in FIG. 24 and FIG. 25. However, the object of copying, storing, etc., one arbitrary image out of the images being displayed, and the copying, storing, etc., is not performed with respect to the other displayed image(s). In order to designate one of the displayed images as an object of the copying, storing, etc., the image is designated with the mouse device, or the like.

For example, by clicking the storage icon 432 using the mouse device, or the like, if the overlay images 440A and 440B are displayed as shown in FIG. 24, a designated one of the overlay images 440A or 440B is copied in the buffer memory of the personal computer 320. Similarly, the half images 460A and 460B are displayed as shown in FIG. 25, a designated one of the half images 460A or 460B is copied in the buffer memory of the personal computer 320 when the storage icon 432 is clicked. Then, the overlay image 440A or 440B or the half image 460A or 460B copied in the buffer memory may be utilized with another application program such as word processing software or with a device, or the like.

By clicking the storage icon 433 using the mouse device, or the like, the overlay image 440A or 440B or the half image 460A or 460B is stored in the recording medium (such as the hard disk 321 or the portable/removable recording medium 311). Then, the overlay image 440A or 440B or the half image 460A or 460B copied in the recording medium may be utilized as an electronic file with another application program such as mailer software or with another device, or the like.

By clicking the deletion icon 434 using the mouse device, or the like, the overlay image 440A or 440B or the half image 460A or 460B is deleted.

By clicking the forward icon 435 using the mouse device, or the like, the image is switched to the next image stored immediately after in the same folder in place of the overlay image 440A or 440B or the half image 460A or 460B. And by clicking the backward icon 436 using the mouse device, or the like, the image is switched to the previous image stored immediately before in the same folder in place of the overlay image 440A or 440B or the half image 460A or 460B.

Figure 26:
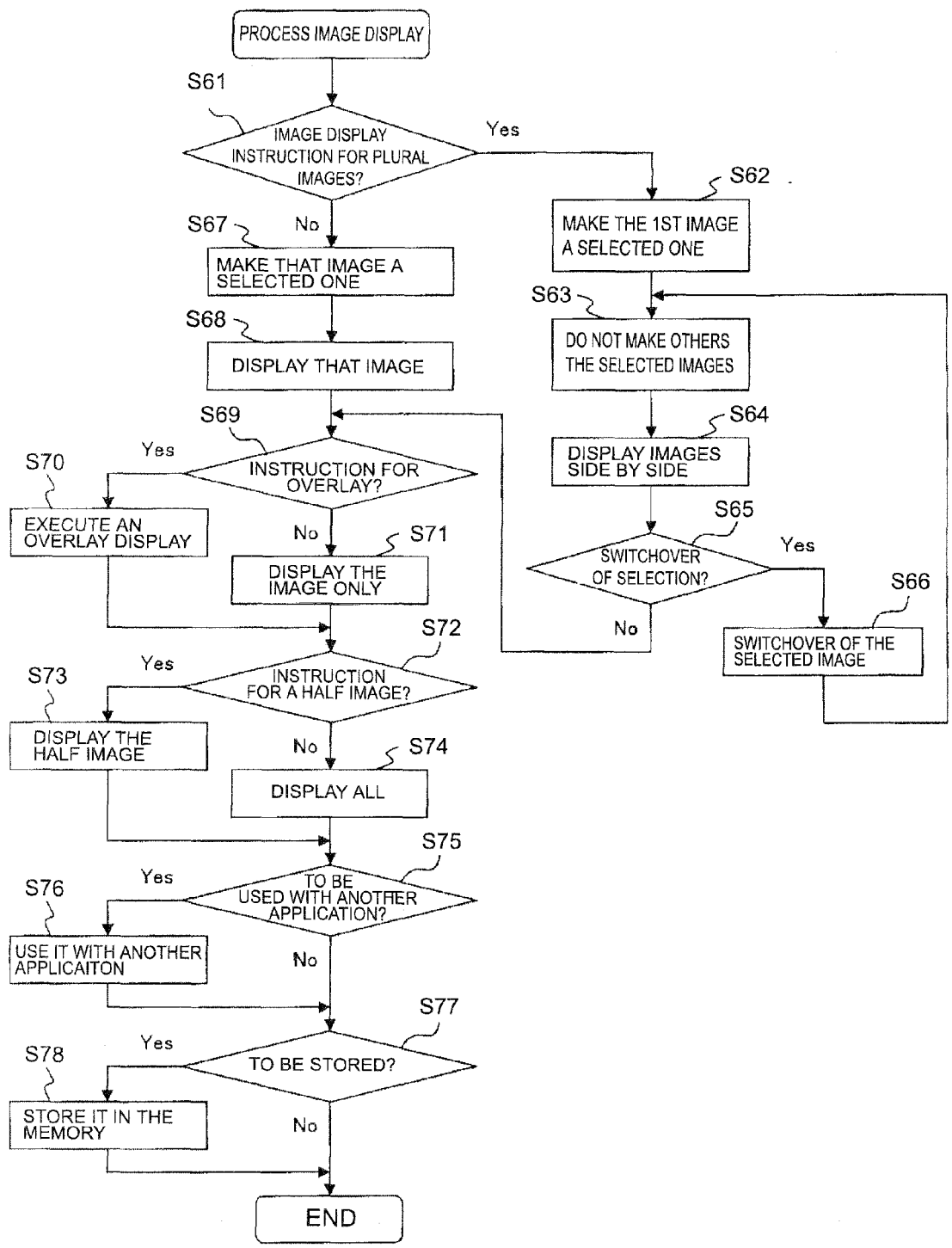
FIG. 26 illustrates a flow of an image display processing.

FIG. 26 illustrates the flow of an image display processing. It can be considered that step S61 of FIG. 26 follows step S51 of FIG. 16, and that the processing shown in FIG. 26 operates in place of step S52 of FIG. 16.

That is, it is determined in step S51 of FIG. 16 whether there has been an instruction to display an image. In step S61, a judgment is made on whether or not the object of the instruction for image display in step S51 of FIG. 16 is a plurality of images, for example two or more images (a maximum of six images is preferred). If it is judged that the object is a plurality of images (Yes in step S61), in step S62, all of the images and incidental information as the objects of the instruction for image display are read out from the recording medium (for example, memory card 311 or hard disk 321), and in step S63, the first image is made a selected image (none of the other images are selected).

In step S64, the plurality of images made the objects of the instruction for image display including the image(s) that is not selected are displayed side by side. Then, in step S65, a judgment is made on whether there has been an instruction to switch the selected image, for example, whether or not an image that is not an object of the selection has been clicked by the mouse device.

If it is judged that there has been a switchover of the selected image (Yes in step S65), in step S66, the selected image is switched, and the process returns to step S63. On the other hand, if it is judged that there has been no switchover of the selected image (No in step S65), the process proceeds to execute step S69.

If it is judged that the object is not a plurality of images (No in step S61), in step S67, the single image that is the object to be displayed is displayed as the selected image in step S68 (corresponding to step S52 in FIG. 16), and the process proceeds to step S69.

Next, a judgment is made in a step S69 on whether or not there has been an instruction by a user for overlay on the image selected at step S67, S62 or S66 for example, by determining whether or not the overlay checkbox 431 is checked. If it is judged that there has been an instruction for overlay (Yes in step S69), in step S70, an overlay display is executed to overlay the overlay information 441. The overlay display herein, however, is executed for all of the images, irrespective of the instruction for selection, even if it is judged that a plurality of images are the object of the instruction for image display in step S61. On the other hand, if it is judged that there has been no instruction for overlay (No in step S69), in step S71, only the image data is displayed without overlaying the overlay information 441.

Next, a judgment is made in a step S72 on whether or not there has been an instruction by a user for a half image to the image selected in step S67, S62 or S66, for example, by determining whether or not the half checkbox 451 is checked. If it is judged that there has been an instruction for a half image (Yes in step S72), in step S73, either a left half or a right half of the stereoscopically measured image 450 (that is, the half image 460) is displayed. The half display herein, however, is executed for all of the images, irrespective of the instruction for selection, even if it is judged that a plurality of images are the object of the instruction for image display in step S61. On the other hand, if it is judged that there has been no instruction for a half image (No in step S72), in step S74, the stereoscopically measured image 450 is displayed.

Next, a judgment is made in step S75 on whether or not a displayed image, for example, a displayed endoscopic image 430, overlay image 440, stereoscopically measured image 450, or the half image 460, is to be utilized with another application program such as word processing software or with another device or the like. If it is judged that the image is to be utilized (Yes in step S75), in step S76, the displayed image is utilized with another application program, or the like. The utilization with the application program or the like herein is, however, for the image selected in step S62 or S66, when a plurality of images are judged to be the object of the instruction for the image display in step S61.

In step S77, a judgment is made on whether or not a displayed image, for example, a displayed endoscopic image 430, overlay image 440, stereoscopically measured image 450, or the half image 460, is to be stored in the recording medium. If it is judged that the image is to be stored (Yes in step S77), in step S78, the displayed image is stored in the recording medium. The storage in the recording medium herein is, however, for the image selected in step S62 or S66, when a plurality of images are judged to be the object of the instruction for the image display in step S61.

While various embodiments of the present invention have been described herein referring to the drawings, it goes without saying that the endoscopic image viewing program and the endoscopic image viewing apparatus to which the invention is applied are not limited to the embodiments described above. For example, the apparatus used to view the images may be either a single apparatus or a system of an integrated apparatus including a plurality of apparatuses, or even a system performing processing via a network such as a LAN or a WAN.

That is, the present invention is not limited to various embodiments as described above and may take various structures or forms within the spirit and scope of the invention.

What is claimed is:

1. A non-transitory computer readable recording medium having a program stored thereon that is executable by a computer to cause the computer to perform a process comprising:
displaying an endoscopic image on a display;
displaying overlay information on the displayed endoscopic image, the overlay information comprising information relating to production of the endoscopic image; and
changing a position of the displayed overlay information relating to production of the endoscopic image in accordance with a change in a manner of displaying the endoscopic image;
wherein the endoscopic image is a stereoscopic image, including right and left images;
wherein the process further comprises changing the displaying of the endoscopic image between displaying both of the right and left images and displaying only one of the right and left images; and
wherein when the displaying of the endoscopic image is changed from displaying both of the right and left images to displaying only one of the right and left images, the position of the displayed overlay information is aligned to be overlapped with the only one of the right and left images that is displayed.

2. The computer readable recording medium according to claim 1, wherein different portions of the overlay information are assigned different priorities, and the displaying of the overlay information comprises displaying all of the overlay information when both of the left and right images are displayed, and displaying only high priority overlay information when only one of the left and right images is displayed.

3. The computer readable recording medium according to claim 1, wherein the process further comprises changing the displaying of the endoscopic image by scrolling the endoscopic image; and
wherein the displaying of the overlay information comprises displaying a first portion of the overlay information such that it is moved with the endoscopic image when the endoscopic image is scrolled, and displaying a second portion of the overlay information such that it is not moved with the endoscopic image when the endoscopic image is scrolled, such that the second portion of the overlay information remains visible on the display.

4. The computer readable recording medium according to claim 3, wherein the scrolling of the right and left images is synchronized.

5. The computer readable recording medium according to claim 4, further comprising displaying one scroll bar, wherein scrolling of each of the right and left images is performed in accordance with operation of the one scroll bar.

6. The computer readable recording medium according to claim 1, wherein different portions of the overlay information are assigned different priorities.

7. The computer readable recording medium according to claim 1, wherein the computer readable recording medium is a portable recording medium.

8. The computer readable recording medium according to claim 1, wherein the computer readable recording medium is provided in a server or host of a website and the program is downloadable by the computer.

9. The computer readable recording medium according to claim 1, further comprising displaying a window including a first area for displaying folders of files hierarchically, a second area for displaying a list of file names of files in a designated one of the folders, and a third area for displaying thumbnail images corresponding to the files in the designated one of the folders.

10. The computer readable recording medium according to claim 9, wherein a boundary between the second and third areas is changeable.

11. The computer readable recording medium according to claim 9, wherein when one of the files is designated in one of the second and third areas, the same file is designated in the other of the second and third areas.

12. The computer readable recording medium according to claim 9, wherein the displaying of the endoscopic image on the display is performed when an instruction is input to the computer to execute a file corresponding to the endoscopic image in the second or third area.

13. The computer readable recording medium according to claim 12, wherein the displaying of the endoscopic image is performed by displaying the endoscopic image in the third area.

14. A non-transitory computer readable recording medium having a program stored thereon that is executable by a computer to cause the computer to perform a process comprising:
displaying an endoscopic image on a display;
displaying overlay information on the displayed endoscopic image, the overlay information comprising information relating to production of the endoscopic image; and
changing the display of the overlay information relating to production of the endoscopic image in accordance with a change in a selection state of the endoscopic image;
wherein the endoscopic image is a stereoscopic image, including right and left images;
wherein the change of the selection state of the endoscopic image is a change between a state in which one of the right and left images is selected and a state in which neither of the left and right images is selected;
wherein when one of the right and left images is selected, only the selected one of the right and left images is displayed, and the one of the right and left images that is not selected is not displayed; and
wherein the changing of the display of the overlay information comprises displaying the overlay information over both the right and left images when neither of the right and left images is selected, and displaying the overlay information over only the selected one of the right and left images, when one of the right and left images is selected.

15. The computer readable recording medium according to claim 14, wherein different portions of the overlay information are assigned different priorities, and the changing of the display of the overlay information comprises displaying all of the overlay information when both of the left and right images are displayed, and displaying only high priority overlay information when only the selected one of the left and right images is displayed.

16. A non-transitory computer readable recording medium having a program stored thereon that is executable by a computer to cause the computer to perform a process comprising:
displaying an endoscopic image on a display;
displaying overlay information on the displayed endoscopic image, the overlay information comprising information relating to production of the endoscopic image; and
changing the display of the overlay information relating to production of the endoscopic image in accordance with a change in a selection state of the endoscopic image;

wherein the endoscopic image is a stereoscopic image, including right and left images;

wherein the change of the selection state of the endoscopic image is a change between a state in which one of the right and left images is selected and a state in which neither of the left and right images is selected; and wherein the changing of the display of the overlay information comprises displaying the overlay information over both the right and left images when neither of the right and left images is selected, and when one of the right and left images is selected, displaying the overlay information on the unselected one of the right and left images and not displaying the overlay information on the selected one of the right and left images.

17. The computer readable recording medium according to claim 16, wherein the changing of the display of the overlay information comprises displaying additional overlay information when one of the right and left images is selected.

18. The computer readable recording medium according to claim 17, wherein the additional overlay information is displayed over the one of the right and left images that is not selected.

19. A method comprising:
displaying an endoscopic image on a display;
displaying overlay information on the displayed endoscopic image, the overlay information comprising information relating to production of the endoscopic image; and
changing a position of the displayed overlay information relating to production of the endoscopic image in accordance with a change in a manner of displaying the endoscopic image
wherein the endoscopic image is a stereoscopic image, including right and left images;
wherein the process further comprises changing the displaying of the endoscopic image between displaying both of the right and left images and displaying only one of the right and left images; and
wherein when the displaying of the endoscopic image is changed from displaying both of the right and left images to displaying only one of the right and left images, the position of the displayed overlay information is aligned to be overlapped with the only one of the right and left images that is displayed.

20. The method according to claim 19, wherein the method is performed by a computer executing a viewing program.

21. The method according to claim 20, wherein the viewing program is required to be installed on the computer in order for the computer to execute the program.

22. The method according to claim 21, further comprising transferring the viewing program to the computer from an endoscopic device which acquired the endoscopic image.

23. The method according to claim 22, wherein the endoscopic device adds a program required for viewing the endoscopic image to image data corresponding to the endoscopic image when the image data is transmitted to the computer or recorded on a recording medium.

24. The method according to claim 23, wherein the program comprises one of the viewing program and a program which is executed by the computer to check whether the viewing program is installed on the computer and to request installation of the viewing program if the viewing program is not installed.

25. The method according to claim 20, wherein the viewing program is not required to be installed on the computer in order for the computer to execute the program.

* * * * *